(12) United States Patent
Baskaran et al.

(10) Patent No.: US 8,889,726 B2
(45) Date of Patent: Nov. 18, 2014

(54) CHEMICA COMPOUNDS

(75) Inventors: Subramanian Baskaran, Research Triangle Park, NC (US); Richard Martin Grimes, Research Triangle Park, NC (US); Wieslaw Mieczyslaw Kazmierski, Research Triangle Park, NC (US); Martin Robert Leivers, Research Triangle Park, NC (US)

(73) Assignee: GlaxoSmithKline LLC, Philadelphia, PA (US)

( * ) Notice: Subject to any disclaimer, the term of this patent is extended or adjusted under 35 U.S.C. 154(b) by 0 days.

(21) Appl. No.: 14/233,396

(22) PCT Filed: Aug. 6, 2012

(86) PCT No.: PCT/US2012/049681
§ 371 (c)(1),
(2), (4) Date: Jan. 17, 2014

(87) PCT Pub. No.: WO2013/022810
PCT Pub. Date: Feb. 14, 2013

(65) Prior Publication Data
US 2014/0171476 A1 Jun. 19, 2014

Related U.S. Application Data

(60) Provisional application No. 61/515,990, filed on Aug. 8, 2011.

(51) Int. Cl.
A61K 31/4178 (2006.01)
C07D 233/54 (2006.01)
C07D 403/14 (2006.01)
C07D 409/14 (2006.01)
C07D 405/14 (2006.01)

(52) U.S. Cl.
CPC ............ *C07D 403/14* (2013.01); *C07D 409/14* (2013.01); *C07D 405/14* (2013.01)
USPC ...................... 514/397; 548/311.7; 548/312.1

(58) Field of Classification Search
USPC ............................. 514/397; 548/311.7, 312.1
See application file for complete search history.

(56) References Cited

FOREIGN PATENT DOCUMENTS

| WO | WO 2010/096462 | 8/2010 |
| WO | WO 2010/111534 | 9/2010 |
| WO | WO 2010/132538 | 11/2010 |
| WO | WO 2011/091446 | 7/2011 |
| WO | WO 2011/091532 | 8/2011 |

*Primary Examiner* — Samantha Shterengarts
(74) *Attorney, Agent, or Firm* — Robert H. Brink

(57) ABSTRACT

Disclosed are compounds of Formula I, Formula II, and Formula III. Also disclosed are salts of the compounds, pharmaceutical composition comprising the compounds or salts, and methods for treating HCV infection by administration of the compounds or salts.

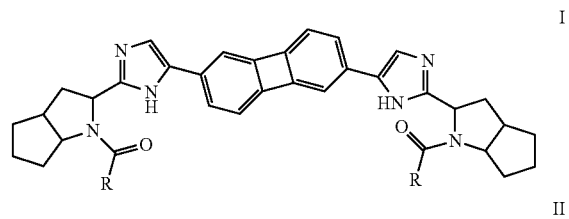

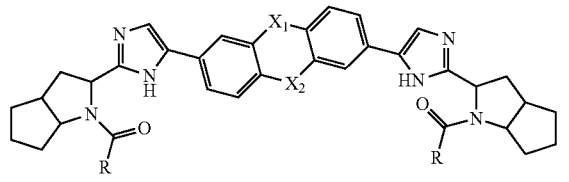

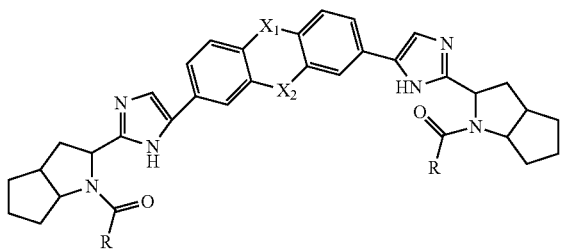

17 Claims, No Drawings

CHEMICA COMPOUNDS

CROSS-REFERENCE TO RELATED APPLICATIONS

This application is filed pursuant to 35 USC 371 as a United States National Phase Application of International Patent Application Serial No. PCT/US2012/049681 filed on Aug. 6, 2012, which claims priority from 61/515,990 filed on Aug. 8, 2011 in the United States.

FIELD OF THE INVENTION

The present disclosure relates to antiviral compounds. In particular, the present disclosure relates to compounds useful for the treatment of hepatitis C virus (HCV) infection, crystalline salts of the compounds, pharmaceutical compositions comprising the compounds, and methods for treating HCV infection.

BACKGROUND OF THE INVENTION

Chronic infection with HCV is a major health problem associated with liver cirrhosis, hepatocellular carcinoma and liver failure. An estimated 170 million chronic carriers worldwide are at risk of developing liver disease. See, for example, Szabo, et al., *Pathol. Oncol. Res.* 2003, 9:215-221, and Hoofnagle J H, *Hepatology* 1997, 26:15S-20S. In the United States alone 2.7 million are chronically infected with HCV, and the number of HCV-related deaths in 2000 was estimated between 8,000 and 10,000, a number that is expected to increase significantly over the next years. Infection by HCV is insidious in a high proportion of chronically infected (and infectious) carriers who may not experience clinical symptoms for many years. Liver cirrhosis can ultimately lead to liver failure. Liver failure resulting from chronic HCV infection is now recognized as a leading cause of liver transplantation.

HCV is a member of the Flaviviridae family of RNA viruses that affect animals and humans. The genome is a single 9.6-kilobase strand of RNA, and consists of one open reading frame that encodes for a polyprotein of ~3000 amino acids flanked by untranslated regions at both 5' and 3' ends (5'- and 3'-UTR). The polyprotein serves as the precursor to at least 10 separate viral proteins critical for replication and assembly of progeny viral particles. The organization of structural and non-structural proteins in the HCV polyprotein is as follows: C-E1-E2-p7-N52-N53-NS4a-NS4b-NS5a-NS5b. Because the replicative cycle of HCV does not involve any DNA intermediate and the virus is not integrated into the host genome, HCV infection can theoretically be cured. While the pathology of HCV infection affects mainly the liver, the virus is found in other cell types in the body including peripheral blood lymphocytes. See, for example, Thomson B J and Finch R G, *Clin Microbial Infect.* 2005, 11:86-94, and Moriishi K and Matsuura Y, *Antivir. Chem. Chemother.* 2003, 14:285-297.

At present, the standard treatment for chronic HCV is interferon alpha (IFN-alpha) in combination with ribavirin and this requires at least six (6) months of treatment. IFN-alpha belongs to a family of naturally occurring small proteins with characteristic biological effects such as antiviral, immunoregulatory and antitumoral activities that are produced and secreted by most animal nucleated cells in response to several diseases, in particular viral infections. IFN-alpha is an important regulator of growth and differentiation affecting cellular communication and immunological control. Treatment of HCV with interferon has frequently been associated with adverse side effects such as fatigue, fever, chills, headache, myalgias, arthralgias, mild alopecia, psychiatric effects and associated disorders, autoimmune phenomena and associated disorders and thyroid dysfunction. Ribavirin, an inhibitor of inosine 5'-monophosphate dehydrogenase (IMPDH), enhances the efficacy of IFN-alpha in the treatment of HCV. Despite the introduction of ribavirin, more than 50% of the patients do not eliminate the virus with the current standard therapy of interferon-alpha (IFN) and ribavirin. By now, standard therapy of chronic hepatitis C has been changed to the combination of pegylated IFN-alpha plus ribavirin. However, a number of patients still have significant side effects, primarily related to ribavirin. Ribavirin causes significant hemolysis in 10-20% of patients treated at currently recommended doses, and the drug is both teratogenic and embryotoxic. Even with recent improvements, a substantial fraction of patients do not respond with a sustained reduction in viral load and there is a clear need for more effective antiviral therapy of HCV infection. See, for example, Fried, et al. *N. Engl. J Med* 2002, 347:975-982.

A number of approaches are being pursued to combat the virus. They include, for example, application of antisense oligonucleotides or ribozymes for inhibiting HCV replication. Furthermore, low-molecular weight compounds that directly inhibit HCV proteins and interfere with viral replication are considered as attractive strategies to control HCV infection. Among the viral targets, the NS3/4A protease/helicase and the NS5b RNA-dependent RNA polymerase are considered the most promising viral targets for new drugs. See, for example, Ni, Z. J. and Wagman, A. S. *Curr. Opin. Drug Discov. Devel.* 2004, 7, 446-459, Beaulieu, P. L. and Tsantrizos, Y. S. *Curr. Opin. Investig. Drugs* 2004, 5, 838-850, and Griffith, et al., *Ann. Rep. Med. Chem* 39, 223-237, 2004.

Besides targeting viral genes and their transcription and translation products, antiviral activity can also be achieved by targeting host cell proteins that are necessary for viral replication. For example, Watashi, et al, Molecular Cell, 19, 111-122, 2005, show how antiviral activity can be achieved by inhibiting host cell cyclophilins. Alternatively, a potent TLR7 agonist has been shown to reduce HCV plasma levels in humans. See, Horsmans, et al, Hepatology, 42, 724-731, 2005.

Compounds said to be useful for treating HCV infection are disclosed, for example, in WO 2008/064218 (Leivers et. al), WO 2008/244380 (Bachand et. al), US 2009/0068140 (Bachand et. al), WO 2010/111534 (Leping et. al), WO 2010/062821 (Schmitz et. al), WO 2011/028596 (Chen et. al), WO 2011/050146 (Baskaran et. al), and WO 2012/018534 (Kozlowski et. al). These references also disclose methods for preparing the compounds, compositions comprising the compounds, pharmaceutical compositions comprising the compounds and additional compounds, methods of treating HCV, salts of the compounds, routes of administration, and other information regarding how to make, formulate, and use the compounds.

Among the compounds disclosed in Leping et. al is the following biphenylene compound.

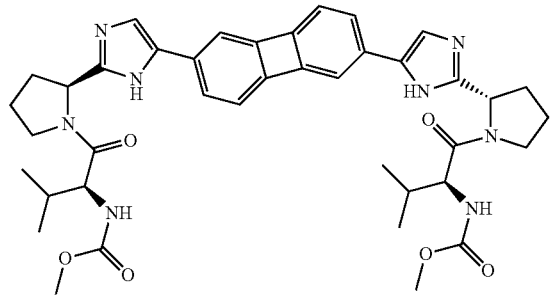 [SMILES: COC(=O)N[C@H](C(=O)N1CCC[C@H]1c1ncc(-c2ccc3c(c2)-c2ccc(-c4cnc([C@@H]5CCCN5C(=O)[C@@H](NC(=O)OC)C(C)C)[nH]4)cc2-3)[nH]1)C(C)C]

SUMMARY OF THE INVENTION

Briefly, in one aspect, the present invention discloses compounds of Formula I;

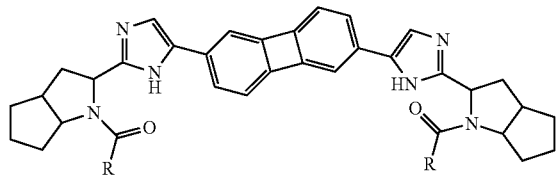

wherein each R is independently —CH($R^1$)—NH—C(O)—$OR^2$;
wherein each $R^1$ is independently —CH(OH)—$CH_3$ or CH($OCH_3$)—$CH_3$; and each $R^2$ is independently $C_{1-3}$alkyl.

Briefly, in another aspect, the present invention discloses compounds of Formula II or Formula III;

II

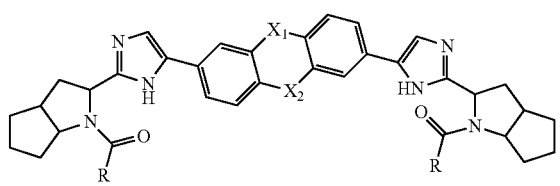

III

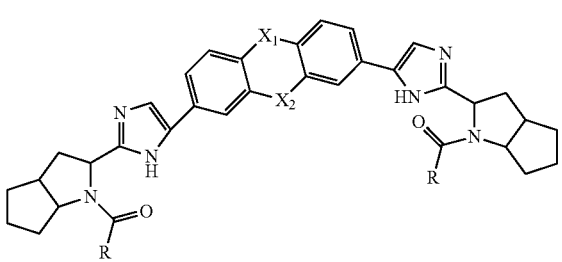

wherein $X^1$ and $X^2$ are independently O, $SO_2$, $NCH_3$, $CF_2$, $CH_2$, $CH_2CH_2$, or a bond (i.e. absent); and
each R is independently —CH($R^1$)—NH—C(O)—$OR^2$;
wherein each $R^1$ is independently CH(OH)—$CH_3$ or CH($OCH_3$)—$CH_3$; and
each $R^2$ is independently $C_{1-3}$alkyl.

In another aspect, the present invention discloses pharmaceutically acceptable salts of the compounds of Formula I.

In another aspect, the present invention discloses pharmaceutical compositions comprising a compound of Formula I or a pharmaceutically acceptable salt thereof.

In another aspect, the present invention discloses pharmaceutically acceptable salts of the compounds of Formula II or Formula III.

In another aspect, the present invention discloses pharmaceutical compositions comprising a compound of Formula II or Formula III or a pharmaceutically acceptable salt thereof.

In another aspect, the present invention discloses a method for treating a viral infection, for example infection with HCV, in a human, comprising administration of a pharmaceutical composition of the invention.

DETAILED DESCRIPTION OF THE INVENTION

Preferably, in the above Formula I, Formula II, and Formula III, each $R^2$ is methyl.

In the above Formula I, Formula II, and Formula III, each R group contains a chiral carbon atom to which $R^1$ is bound. In an embodiment of the invention each R group is enantiomerically enriched with the enantiomer where the chiral carbon has an absolute configuration of S. In the above Formula I, Formula II, and Formula III, each $R^1$ group contains a chiral carbon atom to which an OH or $OCH_3$ group is bound. In an embodiment of the invention each $R^1$ group is enantiomerically enriched with the enantiomer where the chiral carbon in each $R^1$ group has an absolute configuration of R. In addition, there are 3 chiral carbon atoms in each fused bicycle. In an embodiment of the invention, the compounds of Formula I or Formula II or Formula III, or pharmaceutically acceptable salts thereof, are enantiomerically enriched with the enantiomer illustrated below. In general, reference to an enantiomerically enriched compound or salt, is meant to indicate that the specified enantiomer will comprise more than the statistically expected % by weight of the total weight of all enantiomers of the compound or salt. For example, when comparing S and R carbon atoms, a compound is enantiomerically enriched with the S enantiomer of a particular carbon atom if more than 50% of that carbon is S.

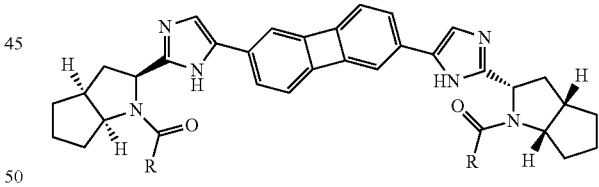

Pharmaceutically acceptable salts can be prepared by methods well known in the art. Suitable salts include those described, for example, in P. Heinrich Stahl, Camille G. Wermuth (eds.), handbook of Pharmaceutical Salts properties, selection, and Use; 2002. See also, WO 2009/020828 (Kim et. Al), which describes the preparation of crystalline salts of certain anti-viral compounds.

The compounds and salts of the invention may be used alone or in combination with one or more other therapeutic agents. In one aspect the further therapeutic agent is selected from Standard of Care therapies such as interferon/ribavarin, small molecule HCV replication inhibitors (more commonly referred to as direct acting antivirals. Suitable combination therapies are described, for example in WO 2008/064218 (Leivers et. al), WO 2008/244380 (Bachand et. al), and US 2009/0068140 (Bachand et. al). These references also contain significant disclosure regarding routes of administration, and other information regarding how to make, formulate, and use the compounds.

EXAMPLES

A table of abbreviations used in this Experimental section is set forth below.

| | |
|---|---|
| ACN | Acetonitrile |
| DCM | Dichloromethane |
| DMF | N,N-dimethylformamide |
| EA | Ethyl acetate |
| HATU | (O-7-azabenzotriazol-1-yl)-N,N,N',N'-tetramethyluronium hexafluorophosphate) |
| ES LC-MS | Electrospray Liquid Chromatography Mass Spectrometry |
| THF | Tetrahydrofuran |
| DIEA | diisopropylethylamine |
| DMSO | dimethylsulfoxide |
| DME | dimethoxyethane |
| TEA | Triethylamine |
| Pd(dppf)Cl$_2$ | 1,1'-Bis(diphenylphosphino)ferrocene-palladium(II)dichloride dichloromethane complex |
| Dess-Martin | Dess-Martin periodinane |
| HRMS | High Resolution Mass Spectroscopy |

The compounds of the present invention may be prepared, for example, as illustrated in the following representative example.

Preparation of Example I

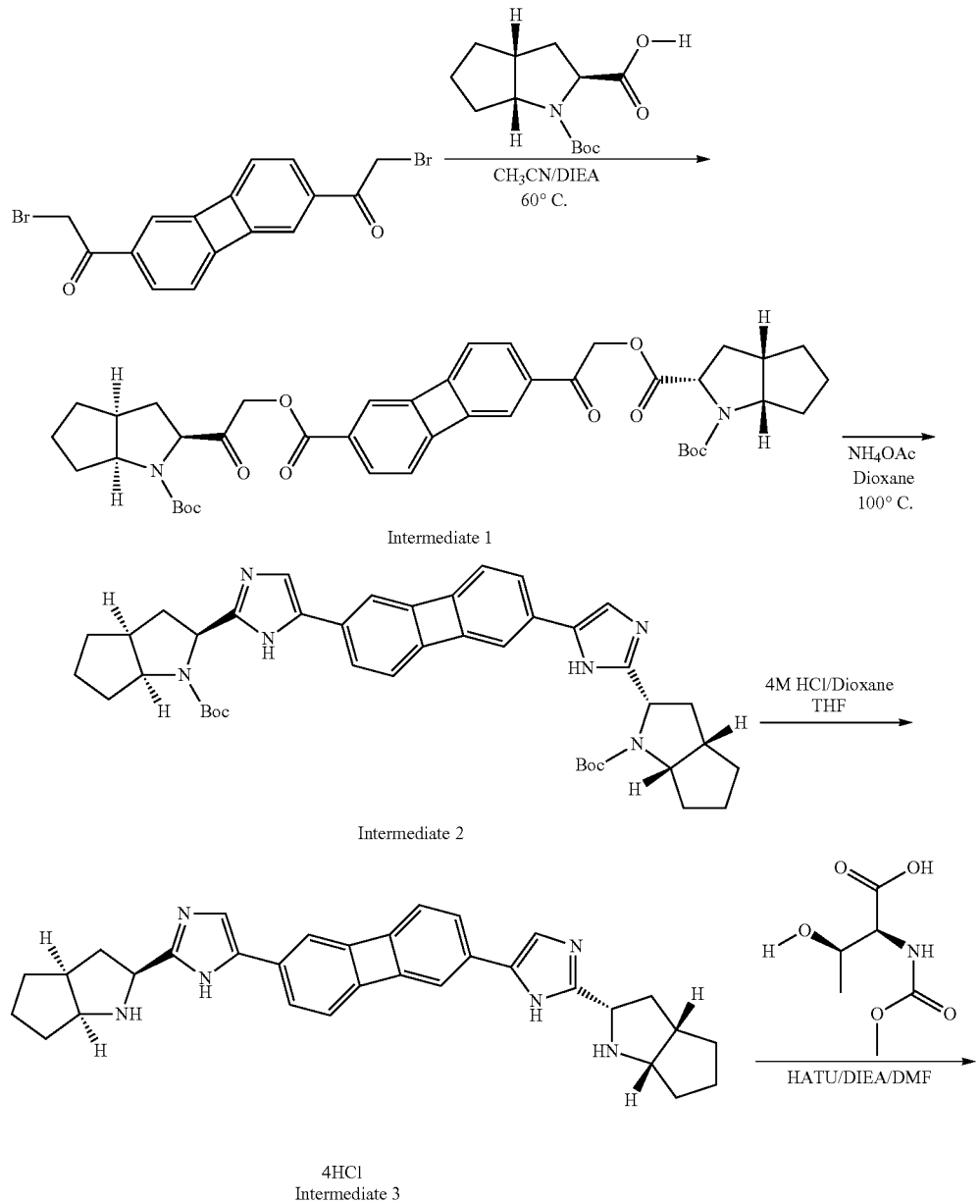

Intermediate 1

Intermediate 2

4HCl
Intermediate 3

-continued

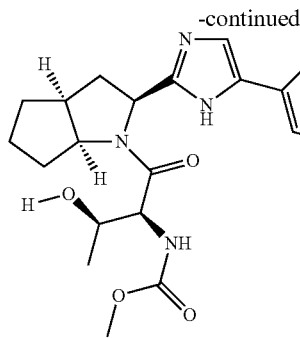 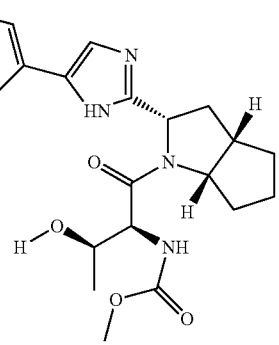

Example 1

Intermediate 1: (2S,2'S,3aS,3a'S,6aS,6a'S)—O'2,O2-(biphenylene-2,6-diylbis(2-oxoethane-2,1-diyl)) 1-di-tert-butyl bis(hexahydrocyclopenta[b]pyrrole-1,2(2H)-dicarboxylate)

1,1'-(2,6-Diphenylenediyl)bis(2-bromoethanone) (1.5 g, 1.90 mmol) was dissolved in Acetonitrile (10 mL). (2S,3aS,6aS)-1-(tert-butoxycarbonyl)octahydrocyclopenta[b]pyrrole-2-carboxylic acid (1.215 g, 4.76 mmol) and DIEA (1 mL, 5.71 mmol) was added and the solution was stirred at 65° C. for 4 h. The solid material was filtered and solvent was evaporated to provide the crude compound which was purified by isco column using 40 g of silica cartridge with hexane/ethyl acetate (increasing gradient from 0% to 100% EA).

Yield: 92%; ES LC-MS m/z=743 (M-FH)+;

1H NMR (400 MHz, DMSO-d 6) δ ppm 7.70 (m, 2H), 7.40 (m, 2H), 7.06 (m, 2H), 5.49 (s, 4H), 4.39 (m, 2H), 4.10 (m, 2H), 2.67 (m, 3H), 2.45 (m, 1H), 2.33 (m, 1H), 1.83-2.02 (m, 3H), 1.73-1.82 (m, 3H), 1.68 (m, 4H), 1.37 (m, 21H).

Intermediate 2: (2S,2'S,3aS,3a'S,6aS,6a'S)-di-tert-butyl 2,2'-(5,5'-(biphenylene-2,6-diyl)bis(1H-imidazole-5,2-diyl))bis(hexahydrocyclopenta[b]pyrrole-1(2H)-carboxylate)

To a stirred solution of (2S,2'S,3aS,3a'S,6aS,6a'S)—O'2,O2-(biphenylene-2,6-diylbis(2-oxoethane-2,1-diyl)) 1-di-tert-butyl bis(hexahydrocyclopenta[b]pyrrole-1,2(2H)-dicarboxylate) (1.3 g, 1.750 mmol, 92% yield) in 1,4-Dioxane (10 mL) in a sealed tube was added ammonium acetate (0.147 g, 1.904 mmol). The reaction mixture was refluxed at 100° C. for 10 h. After cooling down, the solid at the bottom was filtered off and washed with ethyl acetate. The filtrate was evaporated and the residue was purified by flash column using 40 g of silica cartridge with hexane/ethyl acetate (increasing gradient from 0% to 100% EA) to give the product as a brown solid.

Yield: 45%; ES LC-MS m/z=703 (M+H)+;

1H NMR (400 MHz, DMSO-d6) δ ppm 11.43-12.03 (m, 2H), 7.40 (m, 2H), 7.19-7.26 (m, 2H), 7.09-7.17 (m, 2H), 6.69-6.87 (m, 2H), 4.81 (m, 2H), 4.15 (m, 2H), 2.68 (m, 2H), 2.30-2.44 (m, 2H), 1.87-2.02 (m, 3H), 1.83 (m, 3H), 1.63 (m, 4H), 1.45 (m, 9H), 1.28-1.38 (m, 4H), 1.24 (m, 9H).

Intermediate 3: 2,6-bis(2-((2S,3aS,6aS)-octahydrocyclopenta[b]pyrrol-2-yl)-1H-imidazol-5-yl)biphenylene tetrahydrochloride To the (2S,2'S,3aS,3a'S,6aS,6a'S)-di-tert-butyl 2,2'-(5,5'-(biphenylene-2,6-diyl)bis(1H-imidazole-5,2-diyl))bis(hexahydrocyclopenta[b]pyrrole-1(2H)-carboxylate) (500 mg, 0.711 mmol) in Tetrahydrofuran (THF) (2 ml) was slowly added HCl (3.56 ml, 14.23 mmol) in dioxane. The solution was stirred for 12 h at rt and solvent was evaporated, ether (50 mL) was added and the dark brown solid was filtered and dried in house vacuum (2 h) which provided tetra-HCl salt of the amine which was used in the next step without further purification.

Yield: 84%; ES LC-MS m/z=503 (M+H)+;

1H NMR (400 MHz, DMSO-d 6) δppm 10.39 (m, 2H), 9.51 (m, 2H), 7.98 (s, 2H), 7.43 (d, J=7.3 Hz, 2H), 7.31 (s, 2H), 6.96 (d, J=7.3 Hz, 2H), 4.84 (m, 2H), 4.17 (m, 4H), 2.99 (m, 2H), 2.58-2.76 (m, 2H), 2.06 (m, 3H), 1.87-2.00 (m, 1H), 1.75 (m, 2H), 1.65 (m, 6H).

Example 1 dimethyl ((2S,2'S,3R,3'R)-((2S,2'S,3aS,3a'S,6aS,6a'S)-2,2'-(5,5'-(biphenylene-2,6-diyl)bis(1H-imidazole-5,2-diyl))bis(hexahydrocyclopenta[b]pyrrole-2,1(2H)-diyl)bis(3-hydroxy-1-oxobutane-2,1-diyl)) dicarbamate To the crude 2,6-bis(2-((2S,3aS,6aS)-octahydrocyclopenta[b]pyrrol-2-yl)-1H-imidazol-5-yl)biphenylene (80 mg, 0.16 mmol) in N,N-Dimethylformamide (2 ml) was added (2S,3R)-3-hydroxy-2-((methoxycarbonyl)amino)butanoic acid (71 mg, 0.4 mmol), HATU (60.5 mg, 0.16 mmol) and DIEA (0.06 ml, 0.32 mmol), the solution was stirred at rt for 4 h. The reaction was partitioned between ethyl acetate (5 mL) and sat. aq. NaHCO₃ (2 mL). The organic phase was separated and dried over sodium sulphate and evaporated in vacuo to give the crude product which was purified on Gilson-HPLC, eluting with 5 to 80% acetonitrile/water (0.2% NH₃H₂O), to give the pure product.

Yield: 17%; ES LC-MS m/z=821.3 (M+H)+;

1H NMR (400 MHz, DMSO-d6) δ ppm 12.05 (m, 1H), 11.65 (m, 1H), 7.40 (s, 1H), 7.26 (m, 2H), 7.20 (m, 2H), 7.14 (s, 1H), 7.09 (s, 1H), 6.73 (m, 2H), 5.54 (m, 1H), 5.10 (m, 2H), 4.80 (m, 2H), 4.71 (m, 2H), 4.32 (m, 1H), 4.19 (m, 2H), 3.74 (m, 2H), 3.56 (s, 6H), 2.77 (m, 2H), 2.28-2.45 (m, 2H), 2.05 (m, 4H), 1.77 (m, 4H), 1.53 (m, 4H), 0.99-1.13 (m, 7H).

Preparation of Example 2

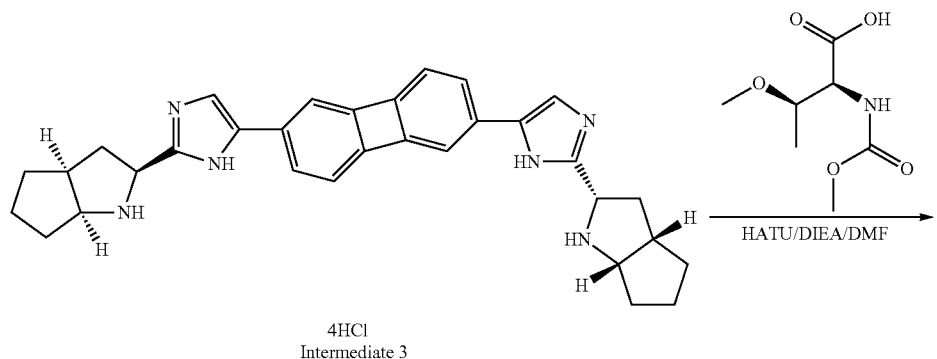

4HCl
Intermediate 3

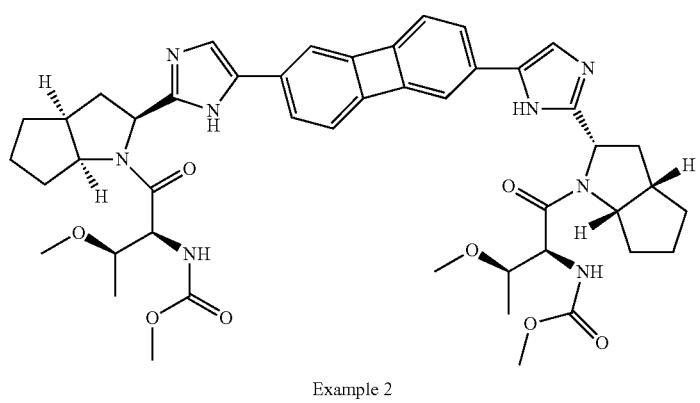

Example 2

Example 2 dimethyl ((2S,2'S,3R,3'R)-((2S,2'S,3aS,3a'S,6aS,6a'S)-2,2'-(5,5'-(biphenylene-2,6-diyl)bis(1H-imidazole-5,2-diyl))bis(hexahydrocyclopenta[b]pyrrole-2,1(2H)-diyl))bis(3-methoxy-1-oxobutane-2,1-diyl)) dicarbamate This example was made similar to the one explained for example 1 using (2S,3R)-3-methoxy-2-((methoxycarbonyl)amino)butanoic acid.

Yield: 12%; ES LC-MS m/z=849.4 (M+H)$^+$;

1H NMR (400 MHz, DMSO-d6) δppm 11.60-12.11 (m, 2H), 7.54 (m, 2H), 7.39 (s, 2H), 7.17 (m, 2H), 7.05-7.13 (m, 2H), 6.94-7.04 (m, 1H), 6.72 (m, 2H), 5.07 (m, 2H), 4.78 (m, 2H), 4.39 (m, 1H), 4.25 (m, 2H), 3.49-3.58 (m, 7H), 3.44 (m, 2H), 3.17-3.22 (m, 6H), 2.75 (m, 2H), 2.29-2.43 (m, 2H), 2.09 (m, 3H), 1.92-2.03 (m, 1H), 1.80-1.89 (m, 2H), 1.68-1.79 (m, 2H), 1.51 (m, 3H), 0.95-1.14 (m, 6H).

Preparation of Example 3

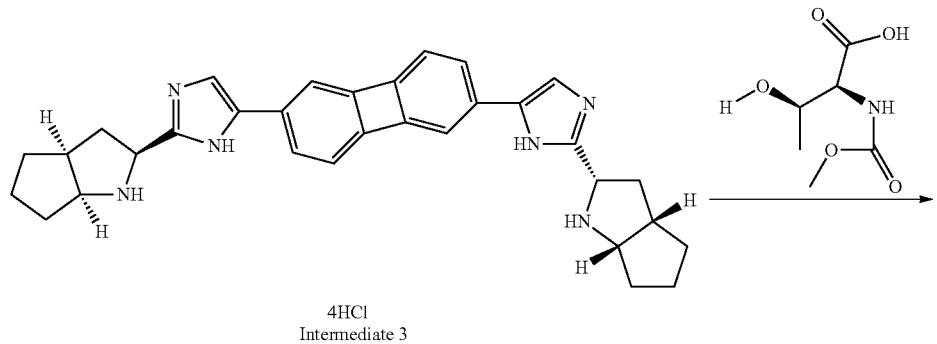

4HCl
Intermediate 3

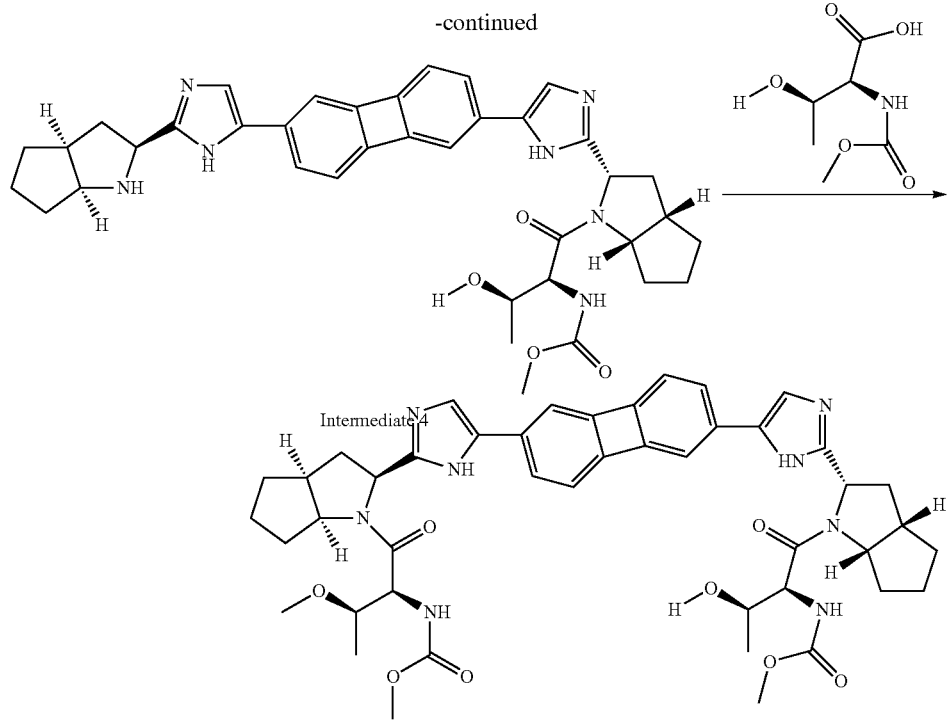

Example 3

Intermediate 4: Methyl ((2S,3R)-3-hydroxy-1-((2S,3aS,6aS)-2-(5-(6-(2-((2S,3aS,6aS)-octahydrocyclopenta[b]pyrrol-2-yl)-1H-imidazol-5-yl)biphenylen-2-yl)-1H-imidazol-2-yl)hexahydrocyclopenta[b]pyrrol-1(2H)-yl)-1-oxobutan-2-yl)carbamate This intermediate was prepared similar to the one explained for example 1 using 1 eq. of (2S,3R)-3-hydroxy-2-((methoxycarbonyl)amino)butanoic acid.

Yield: 18%; ES LC-MS m/z=662.3 (M+H)+;

1H NMR (400 MHz, DMSO-d6) δppm 11.53-12.09 (m, 2H), 7.41 (m, 1H), 7.19 (m, 5H), 6.74 (m, 2H), 5.10 (s, 1H), 4.71 (s, 1H), 4.19 (s, 1H), 3.98 (m, 1H), 3.80-3.93 (m, 1H), 3.67-3.78 (m, 1H), 3.60-3.68 (m, 1H), 3.56 (s, 3H), 2.69 (m, 1H), 2.54-2.60 (m, 2H), 2.35 (m, 2H), 2.19-2.31 (m, 1H), 2.07 (m, 2H), 1.78 (m, 3H), 1.48 (m, 8H), 1.07 (m, 4H).

Example 3

Methyl [(1S,2R)-1-{[(2S,3aS,6aS)-2-[4-(6-{2-[(2S,3aS,6aS)-1-((2S,3R)-3-hydroxy-2-{[(methyloxy)carbonyl]amino}butanoyl)octahydrocyclopenta[b]pyrrol-2-yl]-1H-imidazol-4-yl}-2-biphenylenyl)-1H-imidazol-2-yl]hexahydrocyclopenta[b]pyrrol-1(2H)-yl]carbonyl}-2-(methyloxy)propyl]carbamate This example was made similar to the one explained for example 1 using (2S,3R)-3-methoxy-2-((methoxycarbonyl)amino)butanoic acid.

Yield: 14%; ES LC-MS m/z=835.4 (M+H)+;

1H NMR (400 MHz, DMSO-d6) δppm 11.50-12.15 (m, 2H), 7.55 (m, 1H), 7.41 (s, 1H), 7.19-7.35 (m, 3H), 7.09 (s, 1H), 6.74 (m, 2H), 5.09 (m, 1H), 4.80 (m, 1H), 4.65-4.76 (m, 1H), 4.42 (m, 1H), 4.28 (s, 1H), 4.13-4.25 (m, 1H), 3.82-4.10 (m, 1H), 3.74 (m, 1H), 3.56 (s, 6H), 3.40 (s, 2H), 3.36-3.38 (m, 2H), 3.24-3.32 (m, 2H), 3.17-3.24 (m, 1H), 2.75 (s, 2H), 2.57 (m, 1H), 2.47 (m, 1H), 2.35 (m, 1H), 2.09 (s, 3H), 2.01 (s, 1H), 1.77 (m, 4H), 1.54 (m, 4H), 1.21 (s, 1H), 1.07 (m, 5H).

Preparation of Example 4

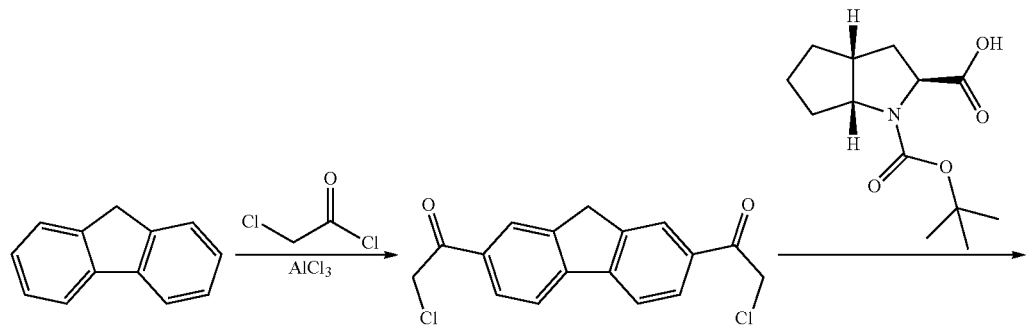

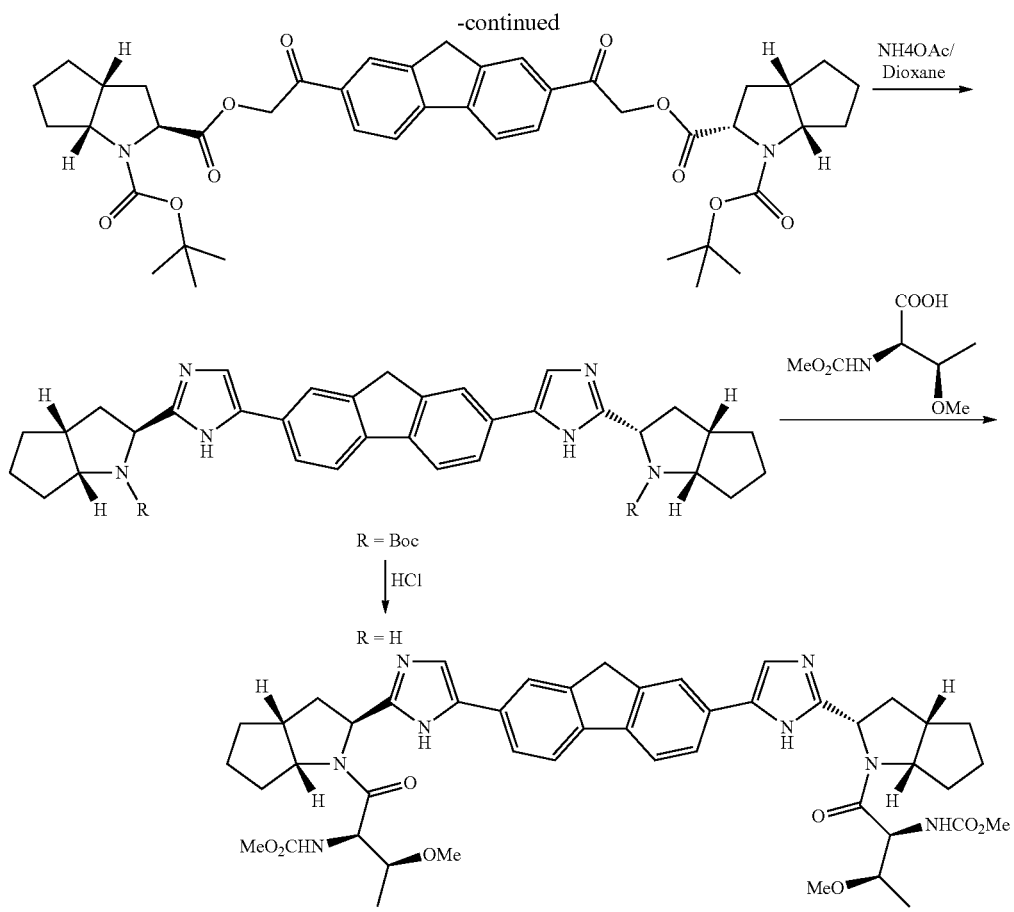

Example 4

1,1'-(9H-fluorene-2,7-diyl)bis(2-chloroethane)

To a stirred solution of 2-chloroacetyl chloride (1.589 mL, 19.97 mmol) and aluminum trichloride (2.66 g, 19.97 mmol) in dichloromethane (DCM) (20 mL) 9H-fluorene (0.83 g, 4.99 mmol) in dichloromethane (DCM) (20 mL) was added dropwise over 5 min at r.t. and left stirring for 2 h. The reaction mixture was then added to a mixture of methanol (50 mL) and H$_2$O (50 mL) chilled to −5° C. The slurry was warmed to ambient, stirred for 30-60 min and the solids collected. The solids were washed well with H$_2$O and dried at 50-60° C. to constant weight.

Yield: 1 g, 54.6%; ES LC-MS m/z=320.7 (M+H$^+$);

1H NMR (400 MHz, DMSO-d6) δppm 8.26 (s, 2H), 8.22 (d, J=8.0 Hz, 2H), 8.09 (d, J=8.0 Hz, 2H), 5.27 (s, 4H), 4.14 (s, 2H)

(2S,2'S,3aS,3a'S,6aS,6a'S)—O'2,O2-((9H-fluorene-2,7-diyl)bis(2-oxoethane-2,1-diyl)) 1-di-tert-butyl bis(hexahydrocyclopenta[b]pyrrole-1,2(2H)-dicarboxylate)

1,1'-(9H-fluorene-2,7-diyl)bis(2-chloroethanone) (1 g, 2.73 mmol), (2S,3aS,6aS)-1-(tert-butoxycarbonyl)octahydrocyclopenta[b]pyrrole-2-carboxylic acid (1.461 g, 5.72 mmol) in acetonitrile (45 mL), and DIPEA (2.86 mL, 16.35 mmol) were mixed and stirred for 6 h at 70° C. The reaction mixture was then filtered to remove the insoluble solids, which were washed with additional acetonitrile (2×5 mL). The organic mixture was reduced to 20 mL and added to briskly stirring H$_2$O (100 mL). The resulting slurry was cooled to 0-5° C., and aged for 2 h. The solids were collected by filtration, washed with H$_2$O, and dried at 50-60° C. to constant weight.

Yield: 2.1 g, 71.3%; ES LC-MS m/z=755.4 (M−H$^+$);

(2S,2'S,3aS,3a'S,6aS,6a'S)-di-tert-butyl 2,2'-(5,5'-(9H-fluorene-2,7-diyl)bis(1H-imidazole-5,2-diyl))bis(hexahydrocyclopenta[b]pyrrole-1(2H)-carboxylate)

To a stirred solution of (2S,2'S,3aS,3a'S,6aS,6a'S)—O'2,O2-((9H-fluorene-2,7-diyl)bis(2-oxoethane-2,1-diyl)) 1-di-tert-butyl bis(hexahydrocyclopenta[b]pyrrole-1,2(2H)-dicarboxylate) (2 g, 1.850 mmol) in dry 1,4-dioxane (18.50 mL) was added ammonium acetate (3.56 g, 46.2 mmol) (25 equiv.). The reaction was refluxed for 6 h. The reaction was cooled slightly then hot filtered and concentrated. This crude material was purified on silica gel eluted with 0-7% 2M ammonia in methanol in DCM. Fractions were concentrated to give the title compound a brown solid.

Yield: 900 mg, 59%; ES LC-MS m/z=715.4(M−H$^+$);

2,7-bis(2-((2S,3aS,6aS)-octahydrocyclopenta[b]pyrrol-2-yl)-1H-imidazol-5-yl)-9H-fluorene, 4 Hydrochloride To a stirred solution of (2S,2'S,3aS,3a'S,6aS,6a'S)-di-tert-butyl 2,2'-(5,5'-(9H-fluorene-2,7-diyl)bis(1H-imidazole-5,2- diyl))bis(hexahydrocyclopenta[b]pyrrole-1(2H)-carboxylate) (900 mg, 1.092 mmol) in dry 1,4-dioxane (10 mL) and methanol (2 mL) was added HCl (4M in 1,4-dioxane, 7.59 mL, 30.4 mmol). The reaction was stirred for 1 h, and then the solid was collected by filtration. The solid was washed twice with 1,4-dioxane and twice with ether. The solid was dried to give a brown solid.

Yield: 600 mg, 83%; ES LC-MS m/z=517.4 (M+H$^+$);

1H NMR (400 MHz, DMSO-d6) δppm 10.60 (br. s., 2H), 10.01 (br. s., 2H), 7.93-8.33 (m, 8H), 4.97 (br. s., 2H), 4.21 (br. s. 2H), 4.10 (s, 2H), 2.91-3.09 (m, 2H), 2.62-2.79 (m, 2H), 1.91-2.22 (m, 6H), 1.73-1.84 (m, 2H), 1.61-1.72 (m, 6H)

Example 4 dimethyl ((2S,2'S,3R,3'R)-((2S,2'S,3aS,3a'S,6aS,6a'S)-2,2'-(5,5'-(9H-fluorene-2,7-diyl)bis(1H-imidazole-5,2-diyl))bis(hexahydrocyclopenta[b]pyrrole-2,1(2H)-diyl))bis(3-methoxy-1-oxobutane-2,1-diyl) dicarbamate To a stirred solution of (2S,3R)-3-methoxy-2-((methoxycarbonyl)amino)butanoic acid (177 mg, 0.928 mmol) in ethanol (5.5 mL) was added DIPEA (0.791 mL, 4.53 mmol) and 2,7-bis(2-((2S,3aS,6aS)-octahydrocyclopenta[b]pyrrol-2-yl)-1H-imidazol-5-yl)-9H-fluorene, 4 hydrochloride (300 mg, 0.453 mmol). This was placed in an ice bath and T3P 50% in ethyl acetate (1.078 mL, 1.811 mmol) was added slowly maintaining the reaction temp below 10° C. The reaction was stirred at 0° C. for 1 h. The reaction was filtered and the ethanol removed from the filtrate by rotary evaporation. The residue was dissolved in EtOAc (20 mL) and washed twice with 1M sodium carbonate, twice with sat ammonium chloride and then brine. The organics were dried over Mg$_2$SO$_4$ and concentrated to give a brown solid. This crude material was purified on silica gel eluted with 0-7% 2M ammonia in methanol to DCM. The desired fractions were combined and concentrated to give a brown solid.

Yield: 65 mg, 15.8%; ES LC-MS m/z=861.6 (M−H$^+$);

1H NMR (400 MHz, DMSO-d6) δppm 11.30-12.49 (m, 2H), 6.93-8.00 (m, 10H), 5.10 (t, J=7.5 Hz, 2H), 4.80 (q, J=7.6 Hz, 2H), 4.33-4.49 (m, 1H), 4.15-4.33 (m, 2H), 3.83-4.03 (m, 2H), 3.50-3.59 (m, 8H), 3.12-3.27 (m, 6H), 2.58-2.82 (m, 2H), 2.30-2.45 (m, 2H), 1.97-2.21 (m, 4H), 1.69-1.95 (m, 4H), 1.43-1.65 (m, 4H), 0.95-1.28 (m, 7H).

Preparation of Example 5

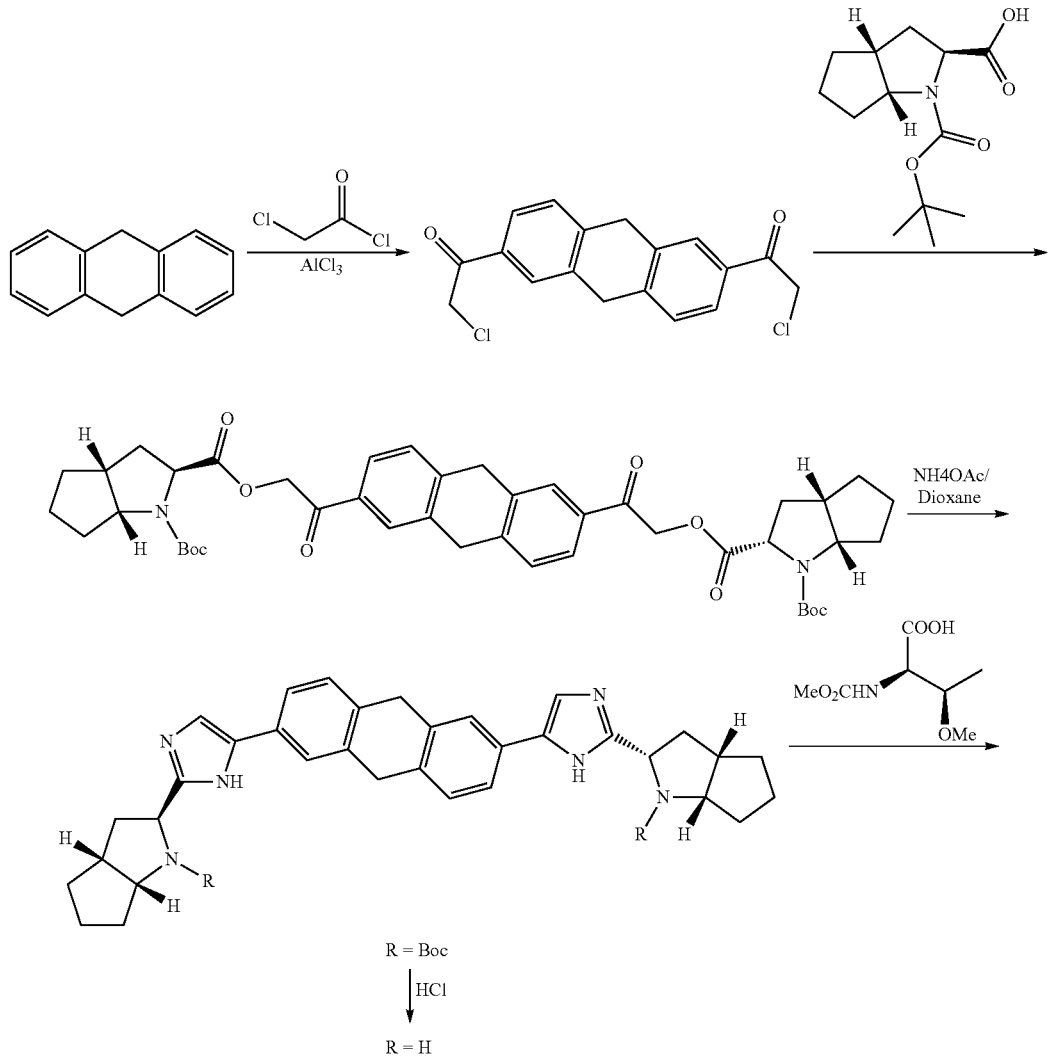

-continued

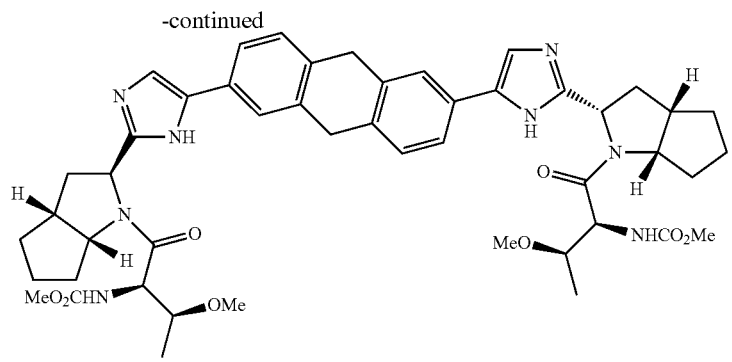

Example 5

1,1'-(9,10-dihydroanthracene-2,6-diyl)bis(2-chloroethanone)

To a stirred solution of 2-chloroacetyl chloride (3.53 mL, 44.4 mmol) and aluminum trichloride (5.92 g, 44.4 mmol) in dichloromethane (DCM) (50 mL), 9,10-dihydroanthracene (2 g, 11.10 mmol) in dichloromethane (DCM) (50 mL) was added dropwise over 5 min at r.t. and left stirring for 1 h. The reaction mixture was then added to a mixture of methanol (100 mL) and $H_2O$ (100 mL) chilled to −5° C. The slurry was warmed to ambient temperature, stirred for 30-60 min. and the solids were collected and were washed well with $H_2O$ and dried at 50-60° C. to constant weight.

Yield: 2.2 g, 58.9%; ES LC-MS m/z=334.9 (M+H$^+$);

1H NMR (400 MHz, DMSO-d6) δppm 7.95 (s, 2H), 7.83 (d, J=7.8 Hz, 2H), 7.52 (d, 2H), 5.17 (s, 4H), 4.08 (s, 4H)

(2S,2'S,3aS,3a'S,6aS,6a'S)-1-di-tert-butyl O'2,O2-((9,10-dihydroanthracene-2,6-diyl)bis(2-oxoethane-2,1-diyl))bis(hexahydrocyclopenta[b]pyrrole-1,2(2H)-dicarboxylate)

1,1'-(9,10-dihydroanthracene-2,6-diyl)bis(2-chloroethanone) (2 g, 6.00 mmol), (2S,3aS,6aS)-1-(tert-butoxycarbonyl)octahydrocyclopenta[b]pyrrole-2-carboxylic acid (3.22 g, 12.60 mmol), and DIPEA (6.29 mL, 36.0 mmol) were mixed in acetonitrile (90 mL) and stirred 6 h at 70° C. The reaction mixture was then filtered to remove the insoluble solids, which were washed with additional acetonitrile (2×10 mL). The organic mixture was reduced to 40 mL and added to $H_2O$ (200 mL). The resulting slurry was cooled to 0-5° C., and aged for 2 h. The solids were collected by filtration, washed with $H_2O$, and dried at 50-60° C. to constant weight.

Yield: 2.5 g, 49.2%; ES LC-MS m/z=769.3 (M−H$^+$);

(2S,2'S,3aS,3a'S,6aS,6a'S)-di-tert-butyl 2,2'-(5,5'-(9,10-dihydroanthracene-2,6-diyl)bis(1H-imidazole-5,2-diyl)bis(hexahydrocyclopenta[b]pyrrole-1(2H)-carboxylate)

To a stirred solution of (2S,3aS,6aS)-2-(2-(6-(2-(((2R,3aS,6aS)-1-(tert-butoxycarbonyl)octahydropentalene-2-carbonyl)oxy)acetyl)-9,10-dihydroanthracen-2-yl)-2-oxoethyl) 1-tert-butyl hexahydrocyclopenta[b]pyrrole-1,2(2H)-dicarboxylate (2.5 g, 2.95 mmol) in dry 1,4-dioxane (29.5 mL) was added ammonium acetate (5.69 g, 73.9 mmol). The reaction was refluxed for 6 h. The reaction was cooled slightly then hot filtered and concentrated. This crude material was purified on silica gel eluted with 0-7% 2M ammonia in methanol in DCM. The fractions that were clean were combined and concentrated to give a brown solid.

Yield: 400 mg, 17.78%; ES LC-MS m/z=731.4(M+H$^+$);

2,6-bis(2-((2S,3aS,6aS)-octahydrocyclopenta[b]pyrrol-2-yl)-1H-imidazol-5-yl)-9,10-dihydroanthracene, 4 Hydrochloride To a stirred solution of (2S,2'S,3aS,3a'S,6aS,6a'S)-di-tert-butyl 2,2'-(5,5'-(9,10-dihydroanthracene-2,6-diyl)bis(1H-imidazole-5,2-diyl))bis(hexahydrocyclopenta[b]pyrrole-1(2H)-carboxylate) (400 mg, 0.547 mmol) in dry 1,4-dioxane (5 mL) and methanol (1 mL) was added HCl (4M in 1,4-dioxane, 3.80 mL, 15.21 mmol). The reaction was stirred for 1 h then the solid was collected by filtration. The solid was washed twice with 1,4-dioxane and twice with ether. The solid was dried to give a yellow solid.

Yield: 250 mg, 66.8%; ES LC-MS m/z=531.4 (M+H$^+$);

1H NMR (400 MHz, DMSO-d6) δppm 10.53 (br. s., 2H), 9.81 (br. s., 2H), 8.12 (s, 2H), 7.90 (s, 2H), 7.76 (d, J=8.2 Hz, 2H), 7.45-7.58 (m, 2H), 4.90 (br. s., 2H), 4.19 (br. s., 2H), 4.02 (s, 4H), 2.90-3.04 (m, 2H), 2.61-2.75 (m, 2H), 1.93-2.17 (m, 6H), 1.73-1.84 (m, 2H), 1.61-1.71 (m, 6H)

Example 5 dimethyl ((2S,2'S,3R,3'R)-((2S,2'S,3aS,3a'S,6aS,6a'S)-2,2'-(5,5'-(9,10-dihydroanthracene-2,6-diyl)bis(1H-imidazole-5,2-diyl))bis(hexahydrocyclopenta[b]pyrrole-2,1(2H)-diyl))bis(3-methoxy-1-oxobutane-2,1-diyl))dicarbamate To a stirred solution of (2S,3R)-3-methoxy-2-((methoxycarbonyl)amino)butanoic acid (130 mg, 0.682 mmol) in Ethanol (5 mL) was added DIPEA (0.581 mL, 3.33 mmol) and 2,6-bis(2-((2S,3aS,6aS)-octahydrocyclopenta[b]pyrrol-2-yl)-1H-imidazol-5-yl)-9,10-dihydroanthracene, 4 Hydrochloride (225 mg, 0.333 mmol). This was placed in an ice bath and T3P 50% in ethyl acetate (0.792 mL, 1.330 mmol) was added slowly maintaining the reaction temp below 10° C. The reaction was stirred at 0° C. for 1 h. The reaction was filtered and the ethanol was removed from the filtrate by rotary evaporation. The residue was dissolved in EtOAc(20 mL) and washed twice with 1M sodium carbonate, twice with sat ammonium chloride and then brine. The organics were dried over $Mg_2SO_4$ and concentrated to give a pale yellow solid. This crude material was purified on silica gel eluted with 0-7% 2M ammonia in methanol to DCM. The desired fractions were combined and concentrated to give a pale yellow solid.

Yield: 29 mg—9.45%; ES LC-MS m/z=875.4 (M–H⁺);
1H NMR (400 MHz, DMSO-d6) δppm 11.96-12.21 (m, 1H), 11.66 (br. s., 1H), 6.93-7.75 (m, 10H), 5.06-5.18 (m, 2H), 4.71-4.89 (m, 2H), 4.16-4.34 (m, 2H), 3.84-3.95 (m, 4H), 3.65 (s, 1H), 3.52-3.60 (m, 9H), 3.24-3.27 (m, 1H), 3.18-3.22 (m, 4H), 2.75 (br. s., 2H), 2.31-2.43 (m, 2H), 1.97-2.20 (m, 4H), 1.70-1.95 (m, 4H), 1.41-1.68 (m, 4H), 0.97-1.27 (m, 7H).
Preparation of Example 6
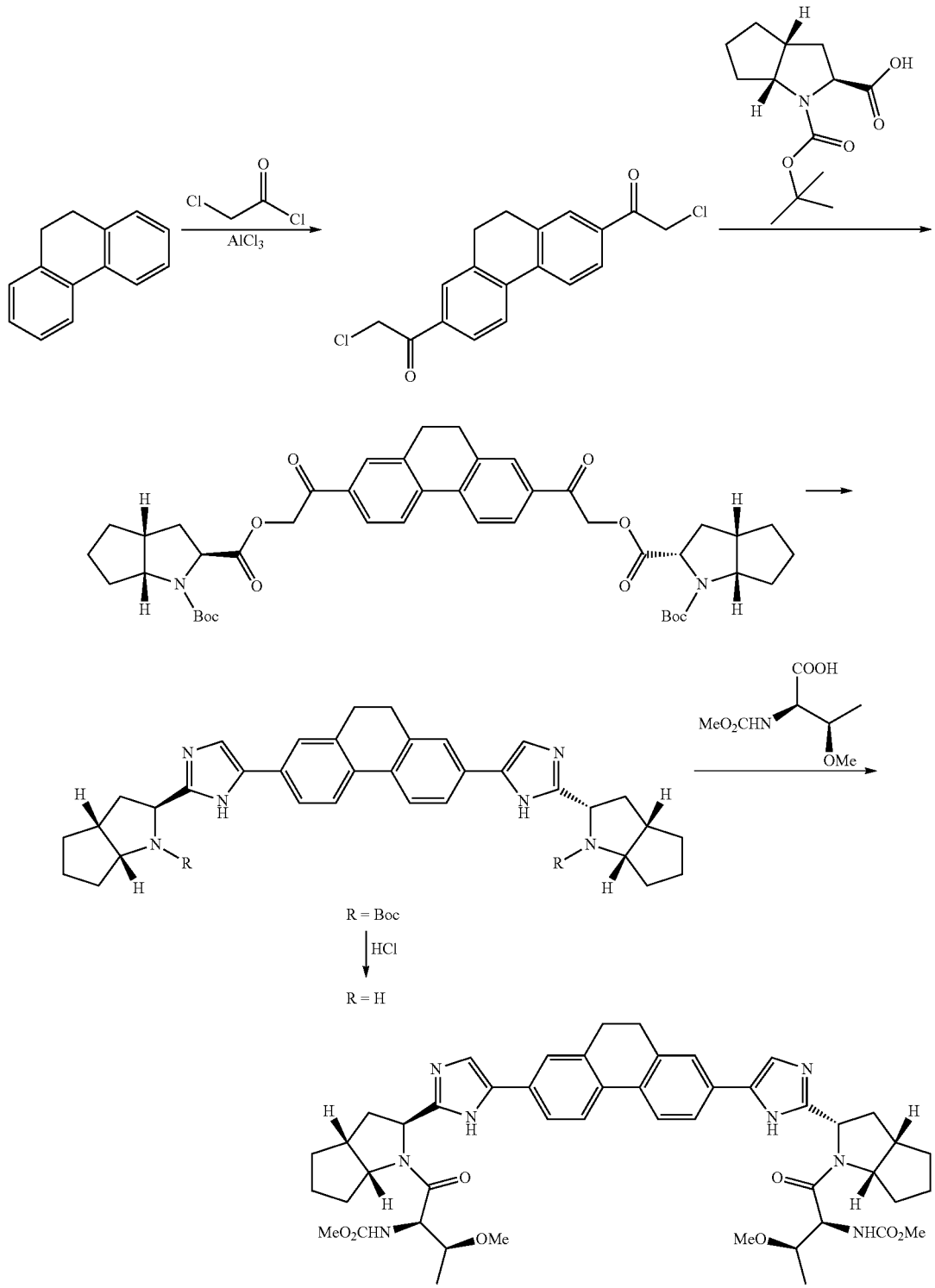
Example 6

1,1'-(9,10-dihydrophenanthrene-2,7-diyl)bis(2-chloroethanone)

To a stirred solution of 2-chloroacetyl chloride (1.765 mL, 22.19 mmol) and aluminum trichloride (2.96 g, 22.19 mmol) in 1,2-dichloroethane (DCE) (20 mL), 9,10-dihydrophenanthrene (1 g, 5.55 mmol) in 1,2-dichloroethane (DCE) (20 mL) was added dropwise over 5 min at r.t. and the reaction mixture was stirred for 1 h at r.t. and 1 h at 60° C. The reaction mixture was cooled to r.t. then added to a mixture of methanol (50 mL) and H$_2$O (50 mL) and chilled to −5° C. The slurry was warmed to ambient, stirred for 30-60 min and the solids collected. The solids were washed well with H$_2$O and dried at 50-60° C. to constant weight.

Yield: 500 mg, 26.5%; ES LC-MS m/z=333.2 (M+H$^+$);

1H NMR (400 MHz, DMSO-d6) δppm 8.09-8.14 (m, 2H), 7.92-7.99 (m, 4H), 5.24 (s, 4H), 2.95 (s, 4H).

(2S,2'S,3aS,3a'S,6aS,6a'S)-1-di-tert-butyl O'2,O2-((9,10-dihydrophenanthrene-2,7-diyl)bis(2-oxoethane-2,1-diyl))bis(hexahydrocyclopenta[b]pyrrole-1,2(2H)-dicarboxylate)

1,1'-(9,10-dihydrophenanthrene-2,7-diyl)bis(2-chloroethanone) (500 mg, 1.501 mmol), (2S,3aS,6aS)-1-(tert-butoxycarbonyl)octahydrocyclopenta[b]pyrrole-2-carboxylic acid (805 mg, 3.15 mmol) and DIPEA (1.572 mL, 9.00 mmol) were mixed in acetonitrile (22 mL), and stirred 6 h at 70° C. The reaction mixture was then filtered to remove the insoluble solids, which were washed with additional acetonitrile (2×5 mL). The organic mixture was reduced to 10 mL. and added to H$_2$O (50 mL). The resulting slurry was cooled to 0-5° C., and aged for 2 h. The solids were collected by filtration, washed with H$_2$O, and dried at 50-60° C. to constant weight.

Yield: 1 g, 86%; ES LC-MS m/z=771.3 (M+H$^+$);

(2S,2'S,3aS,3a'S,6aS,6a'S)-di-tert-butyl 2,2'-(5,5'-(9,10-dihydrophenanthrene-2,7-diyl)bis(1H-imidazole-5,2-diyl)bis(hexahydrocyclopenta[b]pyrrole-1(2H)-carboxylate)

To a stirred solution of (2S,2'S,3aS,3a'S,6aS,6a'S)-1-di-tert-butyl O'2,O2-((9,10-dihydrophenanthrene-2,7-diyl)bis(2-oxoethane-2,1-diyl))bis(hexahydrocyclopenta[b]pyrrole-1,2(2H)-dicarboxylate) (1.0 g, 1.297 mmol) in dry 1,4-dioxane (12.97 mL) was added ammonium acetate (2.500 g, 32.4 mmol) (25 equiv.). The reaction was refluxed for 6 h. The reaction was cooled slightly then hot filtered and concentrated to give a brown solid. This crude material was purified on silica gel eluted with 0-7% 2M ammonia in methanol to DCM. The fractions that were clean were combined and concentrated to give a brown solid.

Yield: 800 mg—81%; ES LC-MS m/z=731.4(M+H$^+$);

2,7-bis(2-((2S,3aS,6aS)-octahydrocyclopenta[b]pyrrol-2-yl)-1H-imidazol-5-yl)-9,10-dihydrophenanthrene, 4 Hydrochloride To a stirred solution of (2S,2'S,3aS,3a'S,6aS,6a'S)-di-tert-butyl 2,2'-(5,5'-(9,10-dihydrophenanthrene-2,7-diyl)bis(1H-imidazole-5,2-diyl))bis(hexahydrocyclopenta[b]pyrrole-1(2H)-carboxylate) (800 mg, 1.094 mmol) in dry 1,4-dioxane (10 mL) and methanol (2.000 mL) was added HCl (4M in 1,4-dioxane, 7.61 mL, 30.4 mmol). The reaction was stirred for 1 h, and then the solid was collected by filtration. The solid was washed twice with 1,4-dioxane and twice with ether and the solid was dried to give a brown solid.

Yield: 600 mg—67.3%; ES LC-MS m/z=529.3 (M+H$^+$);

1H NMR (400 MHz, DMSO-d6) δppm 10.36 (br. s., 1H), 9.49 (br. s., 1H), 8.05 (br. s., 2H), 7.98 (d, J=8.2 Hz, 2H), 7.79-7.87 (m, 4H), 4.83 (br. s., 2H), 4.16 (br. s., 4H), 2.96 (br. s., 2H), 2.91 (s, 4H), 2.62-2.74 (m, 2H), 1.87-2.16 (m, 6H), 1.75 (br. s., 2H), 1.57-1.70 (m, 6H).

Example 6

Dimethyl ((2S,2'S,3R,3'R)-((2S,2'S,3aS,3a'S,6aS,6a'S)-2,2'-(5,5'-(9,10-dihydrophenanthrene-2,7-diyl)bis(1H-imidazole-5,2-diyl))bis(hexahydrocyclopenta[b]pyrrole-2,1(2H)-diyl))bis(3-methoxy-1-oxobutane-2,1-diyl))dicarbamate To a stirred solution of (2S,3R)-3-methoxy-2-((methoxycarbonyl)amino)butanoic acid (174 mg, 0.909 mmol) in ethanol (6 mL) was added DIPEA (0.774 mL, 4.43 mmol) and 2,7-bis(2-((2S,3aS,6aS)-octahydrocyclopenta[b]pyrrol-2-yl)-1H-imidazol-5-yl)-9,10-dihydrophenanthrene, 4 hydrochloride (300 mg, 0.443 mmol). This was placed in an ice bath and T3P 50% in ethyl acetate (1.056 mL, 1.774 mmol) was added slowly maintaining the reaction temp below 10° C. The reaction was stirred at 0° C. for 1 h. The reaction was filtered and the ethanol removed from the filtrate by rotary evaporation. The residue was dissolved in EtOAc (20 mL) and washed twice with 1M sodium carbonate, twice with sat ammonium chloride and then brine. The organics were dried over Mg$_2$SO$_4$ and concentrated to give a pale yellow solid. This crude material was purified on silica gel eluted with 0-7% 2M ammonia in methanol to DCM. The desired fractions were combined and concentrated to give a pale yellow solid.

Yield: 39 mg, 11.96%; ES LC-MS m/z=875.6 (M−H$^+$);

1H NMR (400 MHz, DMSO-d6) δppm 11.99-12.24 (m, 1H), 11.70 (br. s., 1H), 7.43-7.83 (m, 10H), 5.03-5.17 (m, 2H), 4.80 (d, J=7.6 Hz, 2H), 4.33-4.49 (m, 1H), 4.16-4.33 (m, 2H), 3.49-3.58 (m, 9H), 3.17-3.25 (m, 6H), 2.71-2.85 (m, 5H), 2.29-2.43 (m, 2H), 1.97-2.13 (m, 4H), 1.67-1.93 (m, 4H), 1.38-1.66 (m, 4H), 0.95-1.15 (m, 7H).

Preparation of Example 7

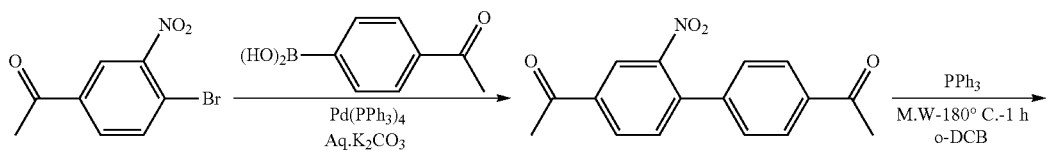

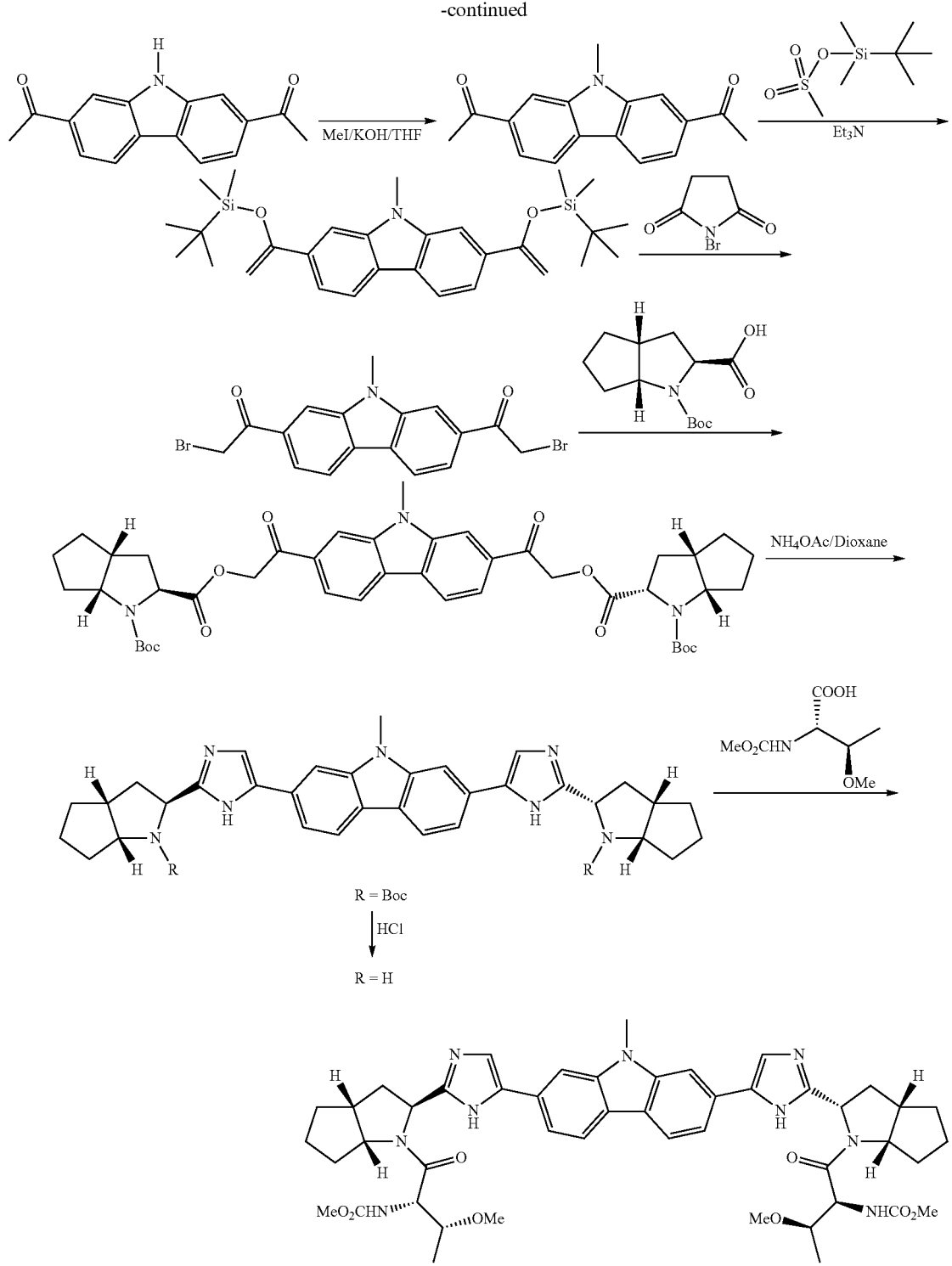

Example 7

1,1'-(2-nitro-[1,1'-biphenyl]-4,4'-diyl)diethanone 1-(4-bromo-3-nitrophenyl)ethanone (2 g, 8.20 mmol) and (4-acetylphenyl)boronic acid (2.016 g, 12.29 mmol), aq.K$_2$CO$_3$ (2M, 12.08 mL, 24.17 mmol) and Pd(PPh$_3$)$_4$ (0.33 g, 0.286 mmol) were dissolved in toluene (40 mL) and heated at 110° C. for 2 days. The crude product was extracted with DCM and purified on silica gel (0-100% EtOAc/Hexane). Fractions were concentrated to give the title compound as a white solid.

Yield: 1.5 g, 64%; ES LC-MS m/z=284.1 (M+H$^+$);

$^1$H NMR (CHLOROFORM-d) δppm 8.45 (d, J=1.8 Hz, 1H), 8.20 (dd, J=8.0, 1.8 Hz, 1H), 8.00-8.05 (m, 2H), 7.54-7.58 (m, 1H), 7.39-7.44 (m, 2H), 2.68 (s, 3H), 2.63 (s, 3H).

1,1'-(9H-carbazole-2,7-diyl)diethanone

The mixture of triphenylphosphine (3.47 g, 13.24 mmol) and 1,1'-(2-nitro-[1,1'-biphenyl]-4,4'-diyl)diethanone (1.5 g, 5.30 mmol) in 1,2-dichlorobenzene (o-DCB) (15.90 mL) was heated at 180° C. under microwave irradiation for 1 h. The reaction mixture was cooled and poured in to the hexane (50 mL). Most of the impurities were removed by precipitation from hexane. The compound was further purified on silica gel ((0-100% EtOAc/Hexane). Fractions were concentrated to give the title compound as a yellow solid.

Yield: 1 g, 74.4%; ES LC-MS m/z=252.1(M+H$^+$);

1H NMR (400 MHz, DMSO-d6) δppm 11.79 (s, 1H), 8.31 (d, J=8.2 Hz, 2H), 8.10-8.18 (m, 2H), 7.81 (dd, J=8.2, 1.4 Hz, 2H), 2.68 (s, 6H).

1,1'-(9-methyl-9H-carbazole-2,7-diyl)diethanone

Iodomethane (0.747 mL, 11.94 mmol) was added to the mixture of 1,1'-(9H-carbazole-2,7-diyl)diethanone (1 g, 3.98 mmol) and potassium hydroxide (0.223 g, 3.98 mmol) in THF (20 mL) and stirred for overnight at room temperature. The solvent was then removed under reduced pressure and the crude was extracted with dichloromethane and washed with water. The organic layer was dried over Na$_2$SO$_4$ and evaporated to get the pure product as yellow solid.

Yield: 1 g, 93%; ES LC-MS m/z=266.1(M+H$^+$);

1H NMR (400 MHz, DMSO-d6) δppm 8.33 (d, J=8.2 Hz, 2H), 8.25 (s, 2H), 7.79-7.87 (m, 2H), 4.03 (s, 3H), 2.71 (s, 6H).

2,7-bis(1-((tert-butyldimethylsilyl)oxy)vinyl)-9-methyl-9H-carbazole

To a mixture of 1,1'-(9-methyl-9H-carbazole-2,7-diyl)diethanone (400 mg, 1.508 mmol) and triethylamine (848 mL, 6034 mmol) in toluene (12 mL), tert-butyldimethylsilyl trifluoromethanesulfonate (1.040 mL, 4.52 mmol) was added at 0° C. The reaction mixture was stirred for 10 min at the same temperature and then stirred for 3 h at room temperature. The reaction mixture was then extracted with ethyl acetate, the organic layer was dried over Na$_2$SO$_4$ and it was concentrated to dryness to give the desired product.

Yield: 700 mg—94%;

1H NMR (CHLOROFORM-d)) δppm 7.95-8.00 (m, 2H), 7.66 (d, J=1.0 Hz, 2H), 7.47-7.51 (m, 2H), 5.03 (d, J=1.6 Hz, 2H), 4.50 (d, J=1.6 Hz, 2H), 3.84 (s, 3H), 1.05 (s, 18H), 0.24 (s, 12H).

1,1'-(9-methyl-9H-carbazole-2,7-diyl)bis(2-bromoethanone)

NBS (505 mg, 2.83 mmol) was added to 2,7-bis(1-((tert-butyldimethylsilyl)oxy)vinyl)-9-methyl-9H-carbazole (700 mg, 1.417 mmol) in THF (20 mL) at 0° C. and the reaction mixture was stirred at same temperature for 30 min. The yellow suspension was filtered and dried to give the desired product.

Yield: 500 mg, 83%;

1H NMR (400 MHz, DMSO-d6) δppm 8.34-8.44 (m, 4H), 7.89 (dd, J=8.3, 1.3 Hz, 2H), 5.10 (s, 4H), 4.06 (s, 4H).

(2S,2'S,3aS,3a'S,6aS,6a'S)-1-di-tert-butyl O'2,O2-((9-methyl-9H-carbazole-2,7-diyl)bis(2-oxoethane-2,1-diyl))bis(hexahydrocyclopenta[b]pyrrole-1,2(2H)-dicarboxylate)

1,1'-(9-methyl-9H-carbazole-2,7-diyl)bis(2-bromoethanone) (500 mg, 1.182 mmol), (2S,3aS,6aS)-1-(tert-butoxycarbonyl)octahydrocyclopenta[b]pyrrole-2-carboxylic acid (634 mg, 2.482 mmol) and DIPEA (1.238 mL, 7.09 mmol) was taken in acetonitrile (20 mL), and was stirred for 3 h at 70° C. The reaction mixture was filtered to remove the insoluble solids, which were washed with additional acetonitrile (2×5 mL). The organic mixture is reduced to 10 mL and added to H$_2$O (50 mL). The resulting slurry is cooled to 0-5° C., and aged for 2 h. The solids were collected by filtration, washed with H$_2$O, and dried at 50-60° C. to constant weight.

Yield: 800 mg, 83%; ES LC-MS m/z=772.6 (M+H$^+$);

(2S,2'S,3aS,3a'S,6aS,6a'S)-di-tert-butyl 2,2'-(5,5'-(9-methyl-9H-carbazole-2,7-diyl)bis(1H-imidazole-5,2-diyl)bis(hexahydrocyclopenta[b]pyrrole-1(2H)-carboxylate)

To a stirred solution of (2S,2'S,3aS,3a'S,6aS,6a'S)-1-di-tert-butyl O'2,O2-((9-methyl-9H-carbazole-2,7-diyl)bis(2-oxoethane-2,1-diyl))bis(hexahydrocyclopenta[b]pyrrole-1,2 (2H)dicarboxylate) (800 mg, 0.985 mmol) in dry 1,4-dioxane (10 mL) was added ammonium acetate (1897 mg, 24.61 mmol) (25 equiv.). The reaction was refluxed for 6 h. The reaction was cooled slightly, filtered and concentrated. This crude material was purified on silica gel eluted with 0-7% 2M ammonia in methanol in DCM. The fractions that were clean were combined and concentrated to give a brown solid.

Yield: 250 mg, 26.4%; ES LC-MS m/z=732.7 (M+H$^+$);

9-methyl-2,7-bis(2-((2S,3aS,6aS)-octahydrocyclopenta[b]pyrrol-2-yl)-1H-imidazol-5-yl)-9H-carbazole, 4 Hydrochloride To a stirred solution of (2S,2'S,3aS,3a'S,6aS,6a'S)-di-tert-butyl 2,2'-(5,5'-(9-methyl-9H-carbazole-2,7-diyl)bis(1H-imidazole-5,2-diyl))bis(hexahydrocyclopenta[b]pyrrole-1 (2H)-carboxylate) (250 mg, 0.260 mmol) in dry 1,4-dioxane (3 mL) and methanol (0.600 mL) was added HCl (4M in 1,4-dioxane, 1.804 mL, 7.22 mmol). The reaction was stirred for 1 h then the solid was collected by filtration. The solid was washed twice with 1,4-dioxane and twice with ether. The solid was dried to give a brown solid.

Yield: 150 mg, 69.9%; ES LC-MS m/z=532.3 (M+H$^+$);

1H NMR (400 MHz, DMSO-d6) δppm 10.39 (br. s., 2H), 9.60 (br. s., 2H), 8.20-8.29 (m, 4H), 8.17 (br. s., 2H), 7.71-7.76 (m, 2H), 4.88 (br. s., 2H), 4.18 (br. s., 2H), 3.94-4.00 (m, 3H), 2.98 (br. s., 2H), 2.63-2.77 (m, 2H), 1.89-2.21 (m, 6H), 1.75 (br. s., 2H), 1.58-1.70 (m, 6H).

Example 7 dimethyl ((2S,2'S,3R,3'R)-((2S,2'S,3aS,3a'S,6aS,6a'S)-2,2'-(5,5'-(9-methyl-9H-carbazole-2,7-diyl)bis(1H-imidazole-5,2-diyl))bis(hexahydrocyclopenta[b]pyrrole-2,1(2H)-diyl))bis(3-methoxy-1-oxobutane-2,1-diyl))dicarbamate To a stirred solution of (2S,3R)-3-methoxy-2-((methoxycarbonyl)amino)butanoic acid (87 mg, 0.454 mmol) in ethanol (3 mL) was added DIPEA (0.387 mL, 2.214 mmol) and 9-methyl-2,7-bis(2-((2S,3aS,6aS)-octahydrocyclopenta[b]pyrrol-2-yl)-1H-imidazol-5-yl)-9H-carbazole, 4 Hydrochloride (150 mg, 0.221 mmol). This was placed in an ice bath and T3P 50% in ethyl acetate (0.527 mL, 0.886 mmol) was added slowly maintaining the reaction temperature below 10° C. The reaction was stirred at 0° C. for 1 h. The reaction was filtered and the ethanol removed from the filtrate by rotary evaporation. The residue was dissolved in EtOAc(10 mL) and washed twice with 1M sodium carbonate, twice with sat ammonium chloride and then brine. The organics were dried over Mg$_2$SO$_4$ and concentrated to give a brown solid. This crude material was purified on silica gel eluted with 0-7% 2M ammonia in methanol to DCM. The desired fractions were combined and concentrated to give a pale yellow solid.

Yield: 25 mg—15.53%; ES LC-MS m/z=876.5 (M−H$^+$);

1H NMR (400 MHz, DMSO-d6) δppm 11.89-12.51 (m, 1H), 11.68 (br. s., 1H), 7.25-8.19 (m, 10H), 4.98-5.22 (m, 2H), 4.70-4.88 (m, 2H), 4.34-4.45 (m, 1H), 4.16-4.33 (m, 2H), 3.77-3.93 (m, 3H), 3.49-3.55 (m, 8H), 3.13-3.24 (m, 6H), 2.62-2.83 (m, 2H), 2.28-2.42 (m, 2H), 1.95-2.21 (m, 4H), 1.66-1.93 (m, 4H), 1.36-1.65 (m, 4H), 0.94-1.19 (m, 7H).

Preparation of Example 8

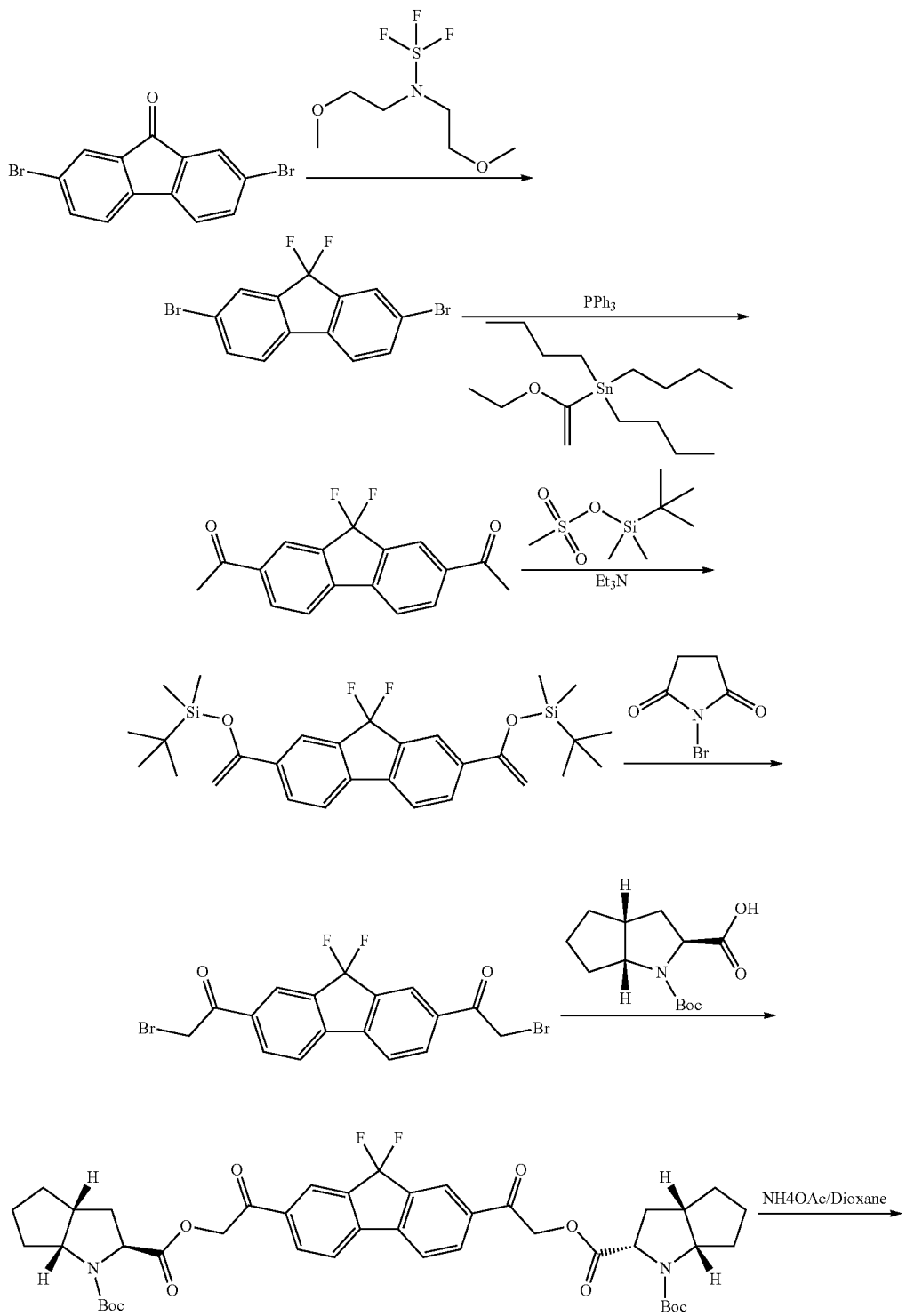

-continued

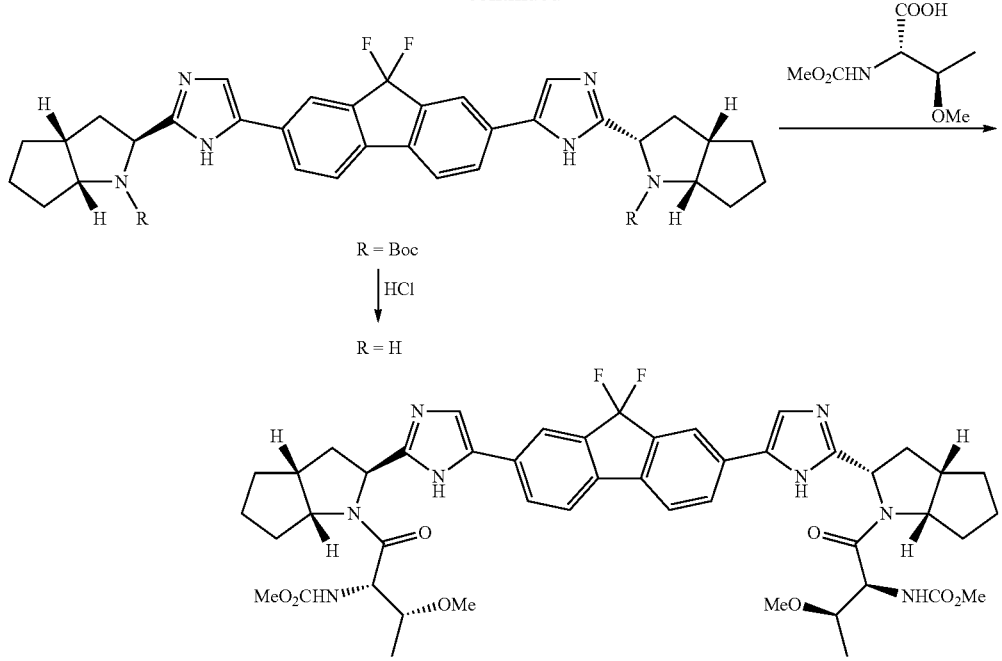

Example 8

2,7-dibromo-9,9-difluoro-9H-fluorene

Deoxofluor (8 mL, 43.4 mmol) was added to 2,7-dibromo-9H-fluoren-9-one (1 g, 2.96 mmol) followed by two drops of ethanol. The reaction mixture was heated at 90° C. for 2 days. The mixture was cooled and poured in to ice water then neutralized with saturated sodium bicarbonate solution. The reaction mixture was extracted with ethyl acetate and washed with saturated sodium bicarbonate solution. The organic layer was dried ($Na_2SO_4$) and concentrated. The crude was purified on silica gel eluted with 0-20% ethyl acetate in hexane. The desired fractions were concentrated to give a white solid.

Yield: 900 mg, 84%;

$^1$H NMR (400 MHz, CHLOROFORM-d) δppm 7.74 (d, J=1.6 Hz, 2H), 7.60 (dd, J=7.7, 1.3 Hz, 2H), 7.41 (d, J=8.2 Hz, 2H).

1,1'-(9,9-difluoro-9H-fluorene-2,7-diyl)diethanone

A mixture of 2,7-dibromo-9,9-difluoro-9H-fluorene (900 mg, 2.500 mmol), Tributyl(1-ethoxyvinyl)tin (3.38 mL, 10.00 mmol) and Pd(Ph$_3$P)$_4$ (289 mg, 0.250 mmol) in 1,4-dioxane (25 mL) were degassed with nitrogen for 10 min then it was heated at 90° C. for overnight under nitrogen. The reaction mixture was cooled to room temperature and 15 mL of 10% HCl was added then stirred for 1 h. The mixture was extracted with ethyl acetate and the organic layer was washed with water and brine. The organics were dried ($Na_2SO_4$) and concentrated. The crude material was purified on silica gel using 0-100% ethyl acetate in hexane. The desired fractions were concentrated to give a white solid.

Yield: 600 mg, 84%; ES LC-MS m/z=287.1(M+H$^+$);

$^1$H NMR (CHLOROFORM-d) δppm 8.22 (d, J=1.0 Hz, 2H), 8.14 (d, J=8.0 Hz, 2H), 7.73 (d, 2H), 2.65 (s, 6H).

(((9,9-difluoro-9H-fluorene-2,7-diyl)bis(ethene-1,1-diyl))bis(oxy))bis(tert-butyldimethyl silane)

To a mixture of 1,1'-(9,9-difluoro-9H-fluorene-2,7-diyl)diethanone (600 mg, 2.096 mmol) and triethylamine (1.178 mL, 8.38 mmol) in toluene (20 mL) tert-butyldimethylsilyl-trifluoromethanesulfonate (1.358 mL, 6.29 mmol) was added at 0° C. The reaction mixture was stirred for 10 min at the same temperature and then stirred for 3 h at room temperature. The reaction mixture was then extracted with ethyl acetate, the organic layer was dried over $Na_2SO_4$ and it was concentrated to dryness to give the desired product.

Yield: 960 mg, 89%;

$^1$H NMR (400 MHz, CHLOROFORM-d) δppm 7.83 (d, J=1.2 Hz, 2H), 7.71 (d, J=8.0 Hz, 2H), 7.49 (d, J=8.0 Hz, 2H), 4.95 (d, J=2.0 Hz, 2H), 4.47 (d, J=2.1 Hz, 2H), 1.00 (s, 18H), 0.21 (s, 12H).

1,1'-(9,9-difluoro-9H-fluorene-2,7-diyl)bis(2-bromoethanone)

NBS (680 mg, 3.82 mmol) was added to (((9,9-difluoro-9H-fluorene-2,7-diyl)bis(ethene-1,1-diyl))bis(oxy))bis(tert-butyldimethylsilane) (0.800 mL, 1.865 mmol) in THF (20 mL) at 0° C. and the reaction mixture was stirred at the same temperature for 1 h. The organic mixture is reduced to 10 mL then the white suspension was filtered and dried to give the desired product.

Yield: 500 mg, 60.4%;

$^1$H NMR (400 MHz, CHLOROFORM-d) δppm 7.95-8.00 (m, 2H), 7.66 (d, J=1.0 Hz, 2H), 7.47-7.51 (m, 2H), 5.03 (d, J=1.6 Hz, 2H), 4.50 (d, J=1.6 Hz, 2H), 3.84 (s, 3H), 1.05 (s, 18H), 0.24 (s, 12H).

(2S,2'S,3aS,3a'S,6aS,6a'S)-1-di-tert-butyl O'2,O2-((9,9-difluoro-9H-fluorene-2,7-diyl)bis(2-oxoethane-2,1-diyl))bis(hexahydrocyclopenta[b]pyrrole-1,2(2H)-dicarboxylate)

1,1'-(9,9-difluoro-9H-fluorene-2,7-diyl)bis(2-bromoethanone) (500 mg, 1.126 mmol), (2S,3aS,6aS)-1-(tert-butoxycarbonyl)octahydrocyclopenta[b]pyrrole-2-carboxylic acid (604 mg, 2.365 mmol) in acetonitrile (20 mL), and DIPEA (1.180 mL, 6.76 mmol) were mixed and stirred for 3 h at 70° C. The reaction mixture was then filtered to remove the insoluble solids, which were washed with additional acetonitrile (2×5 mL). The organic mixture was reduced to 10 mL. and added to briskly stirring H$_2$O (50 mL). The resulting slurry was cooled to 0-5° C., and aged for 2 h. The solids are collected by filtration, washed with H$_2$O, and dried at 50-60° C. to constant weight.

Yield: 800 mg, 89%; ES LC-MS m/z=791.4 (M−H$^+$);

(2S,2'S,3aS,3a'S,6aS,6a'S)-di-tert-butyl 2,2'-(5,5'-(9,9-difluoro-9H-fluorene-2,7-diyl)bis(1H-imidazole-5,2-diyl))bis(hexahydrocyclopenta[b]pyrrole-1(2H)-carboxylate)

To a stirred solution of (2S,2'S,3aS,3a'S,6aS,6a'S)-1-di-tert-butyl O'2,O2-((9,9-difluoro-9H-fluorene-2,7-diyl)bis(2-oxoethane-2,1-diyl))bis(hexahydrocyclopenta[b]pyrrole-1,2(2H)dicarboxylate) (800 mg, 1.009 mmol) in dry 1,4-dioxane (10 mL) was added ammonium acetate (1.944 g, 25.2 mmol) (25 equiv.). The reaction was refluxed for 6 h. The reaction was cooled slightly then hot filtered and concentrated. This crude material was purified on silica gel eluted with 0-7% 2M ammonia in methanol in DCM. The fractions that were clean were combined and concentrated to give a brown solid.

Yield: 350 mg, 41.5%; ES LC-MS m/z=753.4 (M+H$^+$);

(2S,2'S,3aS,3a'S,6aS,6a'S)-2,2'-(5,5'-(9,9-difluoro-9H-fluorene-2,7-diyl)bis(1H-imidazole-5,2-diyl))bis(octahydrocyclopenta[b]pyrrole), 4 Hydrochloride To a stirred solution of (2S,2'S,3aS,3a'S,6aS,6a'S)-di-tert-butyl 2,2'-(5,5'-(9,9-difluoro-9H-fluorene-2,7-diyl)bis(1H-imidazole-5,2-diyl))bis(hexahydrocyclopenta[b]pyrrole1(2H)-carboxylate) (350 mg, 0.465 mmol) in dry 1,4-dioxane (3 mL) and methanol (0.600 mL) was added HCl (4M in 1,4-dioxane, 3.23 mL, 12.92 mmol). The reaction was stirred for 1 h then the solid was collected by filtration. The solid was washed twice with 1,4-dioxane and twice with ether. The solid was dried to give a brown solid.

Yield: 150 mg, 44.8%; ES LC-MS m/z=551.2 (M−H$^+$);

Example 8

Dimethyl ((2S,2'S,3R,3'R)-((2S,2'S,3aS,3a'S,6aS,6a'S)-2,2'-(5,5'-(9,9-difluoro-9H-fluorene-2,7-diyl)bis(1H-imidazole-5,2-diyl))bis(hexahydrocyclopenta[b]pyrrole-2,1(2H)-diyl))bis(3-methoxy-1-oxobutane-2,1-diyl))dicarbamate To a stirred solution of (2S,3R)-3-methoxy-2-((methoxycarbonyl)amino)butanoic acid (46.0 mg, 0.241 mmol) in ethanol (3 mL) was added DIPEA (0.205 mL, 1.174 mmol) and (2S,2'S,3aS,3a'S,6aS,6a'S)-2,2'-(5,5'-(9,9-difluoro-9H-fluorene-2,7-diyl)bis(1H-imidazole-5,2-diyl))bis(octahydrocyclopenta[b]pyrrole), 4 Hydrochloride (100 mg, 0.117 mmol). This was placed in an ice bath and T3P 50% in ethyl acetate (0.279 mL, 0.470 mmol) was added slowly maintaining the reaction temp below 10° C. The reaction was stirred at 0° C. for 1 h. The reaction was filtered and the ethanol removed from the filtrate by rotary evaporation. The residue was dissolved in EtOAc(10 mL) and washed twice with 1M sodium carbonate, twice with sat ammonium chloride and then brine. The organics were dried over Mg$_2$SO$_4$ and concentrated to give a brown solid. This crude material was purified on silica gel eluted with 0-7% 2M ammonia in methanol in DCM. The desired fractions that were clean were combined and concentrated to give a pale yellow solid.

Yield: 8 mg, 6.97%; ES LC-MS m/z=897.4 (M−H$^+$);

1H NMR (400 MHz, DMSO-d6) δppm 11.73-12.46 (m, 2H), 7.36-8.04 (m, 10H), 5.07 (t, J=7.5 Hz, 2H), 4.78 (q, J=7.6 Hz, 2H), 4.14-4.45 (m, 2H), 3.46-3.54 (m, 7H), 3.14-3.22 (m, 6H), 2.60-2.83 (m, 2H), 2.28-2.39 (m, 2H), 2.01-2.19 (m, 3H), 1.90-2.01 (m, 2H), 1.66-1.90 (m, 4H), 1.54 (br. s., 3H), 1.38-1.47 (m, 2H), 0.93-1.13 (m, 7H).

Preparation of Example 9

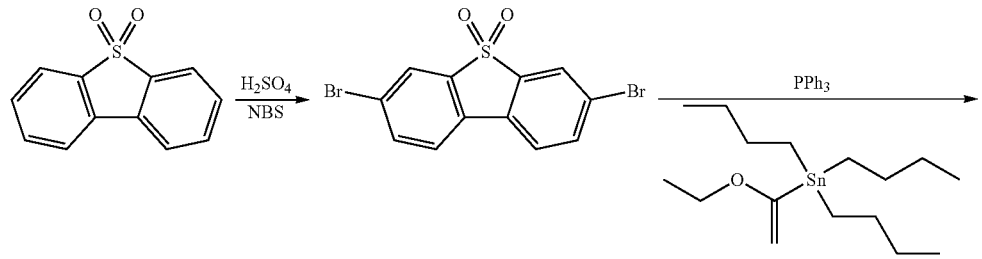

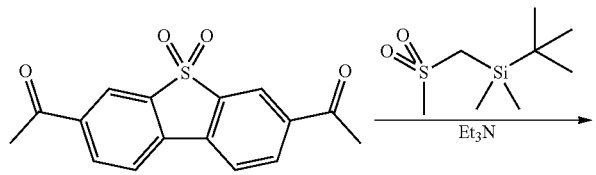

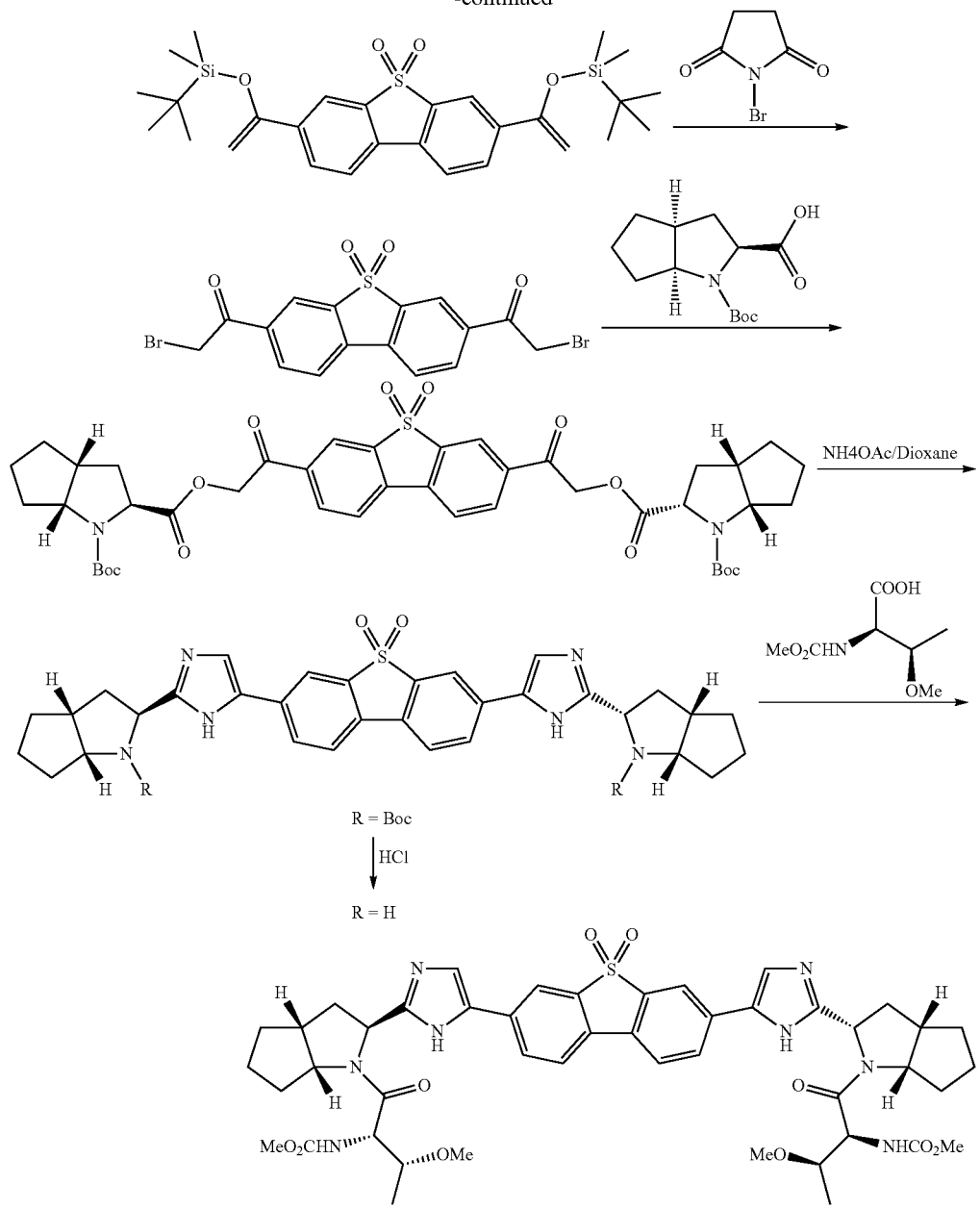

Example 9

3,7-dibromodibenzo[b,d]thiophene 5,5-dioxide

To a solution of dibenzo[b,d]thiophene 5,5-dioxide (2 g, 9.25 mmol) in conc. $H_2SO_4$ (60 mL) was added NBS (3.29 g, 18.50 mmol) at room temperature. After 24 h, the solution was poured into ice water carefully. Colorless solids were filtrated and washed with water and methanol. The obtained solids were recrystallized from chlorobenzene to afford colorless needles.

Yield: 1.6 g, 44.9%;

1H NMR (400 MHz, DMSO-d6) δppm 8.33 (d, J=1.8 Hz, 2H), 8.11-8.16 (m, 2H), 7.99 (dd, J=8.2, 1.8 Hz, 2H).

1,1'-(5,5-dioxidodibenzo[b,d]thiophene-3,7-diyl) diethanone

A mixture of 3,7-dibromodibenzo[b,d]thiophene 5,5-dioxide (600 mg, 1.604 mmol), Tributyl(1-ethoxyvinyl)tin (2.251 mL, 6.67 mmol) and $Pd(Ph_3P)_4$ (185 mg, 0.160 mmol) in 1,4-dioxane (15 mL) were degassed with nitrogen for 10 min then it was heated at 90° C. for overnight under nitrogen. The reaction mixture was cooled to room temperature and 15 mL of 10% HCl was added then stirred for 1 h. The mixture was extracted with ethyl acetate and the organic layer was washed with water and brine. The organics were dried ($Na_2SO_4$) and concentrated. The crude material was purified on silica gel using 0-100% ethyl acetate in hexane. The desired fractions were concentrated to give a white solid.

Yield: 400 mg, 81%;
¹H NMR (CHLOROFORM-d) δppm 8.39 (d, J=1.2 Hz, 2H), 8.28 (dd, J=8.0, 1.6 Hz, 2H), 7.96 (d, 2H), 2.68 (s, 6H).

3,7-bis(1-((tert-butyldimethylsilyl)oxy)vinyl)dibenzo [b,d]thiophene 5,5-dioxide To a mixture of 1,1'-(5,5-dioxidodibenzo[b,d]thiophene-3, 7-diyl)diethanone (350 mg, 1.165 mmol) and triethylamine (0.655 mL, 4.66 mmol) in toluene (12 mL), tert-butyldimethylsilyl trifluoromethanesulfonate (0.804 mL, 3.50 mmol) was added at 0° C. The reaction mixture was stirred for 10 min at the same temperature and then stirred for 3 h at room temperature. The reaction mixture was then extracted with ethyl acetate, the organic layer was dried over $Na_2SO_4$ and it was concentrated to dryness to give the desired product.
Yield: 600 mg, 95%; ES LC-MS m/z=529.2(M+H⁺);
¹H NMR (400 MHz, CHLOROFORM-d) δppm 8.02 (d, J=1.2 Hz, 2H), 7.86 (dd, J=8.1, 1.7 Hz, 2H), 7.72 (d, J=8.0 Hz, 2H), 5.01 (d, J=2.3 Hz, 2H), 4.56 (d, J=2.3 Hz, 2H), 1.01 (s, 18H), 0.23 (s, 12H).

1,1'-(5,5-dioxidodibenzo[b,d]thiophene-3,7-diyl)bis (2-bromoethanone)

NBS (404 mg, 2.269 mmol) was added to 3,7-bis(1-((tert-butyldimethylsilyl)oxy)vinyl)dibenzo[b,d]thiophene 5,5-dioxide (600 mg, 1.135 mmol) in THF (15 mL) at 0° C. and the reaction mixture was stirred at the same temperature for 1 h. The white suspension was filtered and dried to give the desired product. The product was not purified further.
Yield: 350 mg, 68.7%;
1H NMR (400 MHz, DMSO-d6) δppm 8.34-8.44 (m, 4H), 7.89 (dd, J=8.3, 1.3 Hz, 2H), 5.10 (s, 4H), 4.06 (s, 4H).

(2S,2'S,3aS,3a'S,6aS,6a'S)-1-di-tert-butyl O'2,O2-((5,5-dioxidodibenzo[b,d]thiophene-3,7-diyl)bis(2-oxoethane-2,1-diyl))bis(hexahydrocyclopenta[b] pyrrole-1,2(2H)-dicarboxylate)

1,1'-(5,5-dioxidodibenzo[b,d]thiophene-3,7-diyl)bis(2-bromoethanone) (350 mg, 0.764 mmol), (2S,3aS,6aS)-1-(tert-butoxycarbonyl)octahydrocyclopenta[b]pyrrole-2-carboxylic acid (410 mg, 1.604 mmol) in acetonitrile (15 mL), and DIPEA (0.801 mL, 4.58 mmol) were mixed and stirred for 3 h at 70° C. The reaction mixture was then filtered to remove the insoluble solids, which were washed with additional acetonitrile (2×5 mL). The organic mixture was reduced to ~10 mL and added to briskly stirring $H_2O$ (50 mL). The resulting slurry was cooled to 0-5° C., and aged for 2 h. The solids were collected by filtration, washed with $H_2O$, and dried at 50-60° C. to constant weight.
Yield: 600 mg, 92%; ES LC-MS m/z=805.3 (M–H⁺);
1H NMR (400 MHz, DMSO-d6) δppm 8.62 (d, J=19.0 Hz, 2H), 8.48 (d, J=8.0 Hz, 2H), 8.36 (d, J=8.2 Hz, 2H), 5.42-5.79 (m, 4H), 4.31-4.46 (m, 2H), 3.98-4.14 (m, 2H), 2.66 (br. s., 2H), 1.53-1.97 (m, 12H), 1.34 (d, J=9.6 Hz, 22H).

(2S,2'S,3aS,3a'S,6aS,6a'S)-di-tert-butyl 2,2'-(5,5'-(5, 5-dioxidodibenzo[b,d]thiophene-3,7-diyl)bis(1H-imidazole-5,2-diyl))bis(hexahydrocyclopenta[b]pyr-role-1(2H)-carboxylate)

To a stirred solution of (2S,2'S,3aS,3a'S,6aS,6a'S)-1-di-tert-butyl O'2,O2-((5,5-dioxidodibenzo[b,d]thiophene-3,7-diyl)bis(2-oxoethane-2,1-diyl))bis(hexahydrocyclo penta[b] pyrrole-1,2(2H)-dicarboxylate) (600 mg, 0.706 mmol) in dry 1,4-dioxane (10 mL) was added ammonium acetate (1361 mg, 17.66 mmol) (25 equiv.). The reaction was refluxed for 6 h. The reaction was cooled slightly then hot filtered and concentrated. This crude material was purified on silica gel eluted with 0-7% 2M ammonia in methanol in DCM. The fractions that were clean were combined and concentrated to give a pale yellow solid.
Yield: 250 mg, 40.6%; ES LC-MS m/z=765.3(M–H⁺);

3,7-bis(2-((2S,3aS,6aS)-octahydrocyclopenta[b]pyr-rol-2-yl)-1H-imidazol-5-yl)dibenzo[b,d]thiophene 5,5-dioxide, 4 Hydrochloride To a stirred solution of (2S,2'S,3aS,3a'S,6aS,6a'S)-di-tert-butyl 2,2'-(5,5'-(5,5-dioxidodibenzo[b,d]thiophene-3,7-diyl) bis(1H-imidazole-5,2-diyl))bis(hexahydrocyclo penta[b] pyrrole-1(2H)-carboxylate) (250 mg, 0.326 mmol) in dry 1,4-dioxane (3 mL) and methanol (0.600 mL) was added HCl (4M in 1,4-dioxane, 2.265 mL, 9.06 mmol). The reaction was stirred for 1 h then the solid was collected by filtration. The solid was washed twice with 1,4-dioxane and twice with ether. The solid was dried to give a pale yellow solid.
Yield: 100 mg, 32.3%; ES LC-MS m/z=565.2 (M–H⁺);

Example 9 dimethyl a2S,2'S,3R,3'R)-((2S,2'S,3aS,3a'S,6aS, 6a'S)-2,2'-(5,5'-(5,5-dioxidodibenzo[b,d]thiophene-3, 7-diyl)bis(1H-imidazole-5,2-diyl))bis(hexahydrocy-clopenta[b]pyrrole-2,1(2H)-diyl))bis(3-methoxy-1-oxobutane-2,1-diyl))dicarbamate To a stirred solution of (2S,3R)-3-methoxy-2-((methoxy-carbonyl)amino)butanoic acid (55.0 mg, 0.288 mmol) in Ethanol (3 mL) was added DIPEA (0.245 mL, 1.403 mmol) and 3,7-bis(2-((2S,3aS,6aS)-octahydrocyclopenta[b]pyrrol-2-yl)-1H-imidazol-5-yl)dibenzo[b,d]thiophene 5,5-dioxide, 4 Hydrochloride (100 mg, 0.140 mmol). This was placed in an ice bath and T3P 50% in ethyl acetate (0.334 mL, 0.561 mmol) was added slowly maintaining the reaction temp below 10° C. The reaction was stirred at 0° C. for 1 h. The reaction was filtered and the ethanol removed from the filtrate by rotary evaporation. The residue was dissolved in EtOAc (10 mL) and washed twice with 1M sodium carbonate, twice with sat ammonium chloride and then brine. The organics were dried over $Mg_2SO_4$ and concentrated to give a brown solid. This crude material was purified on silica gel eluted with 0-7% 2M ammonia in methanol to DCM. The desired fractions were combined and concentrated to give a pale yellow solid.
Yield: 9 mg, 10.43%; ES LC-MS m/z=911.2 (M–H⁺);
1H NMR (400 MHz, DMSO-d6) δppm 11.60-12.73 (m, 2H), 7.46-8.38 (m, 10H), 4.99-5.16 (m, 2H), 4.72-4.84 (m, 2H), 4.22-4.47 (m, 2H), 3.49-3.54 (m, 6H), 3.38-3.48 (m, 2H), 3.14-3.24 (m, 6H), 2.59-2.83 (m, 2H), 2.31-2.42 (m, 2H), 2.10 (br. s., 3H), 1.90-2.00 (m, 1H), 1.67-1.89 (m, 4H), 1.35-1.66 (m, 5H), 0.88-1.10 (m, 7H).

Preparation of Example 10
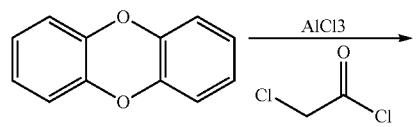
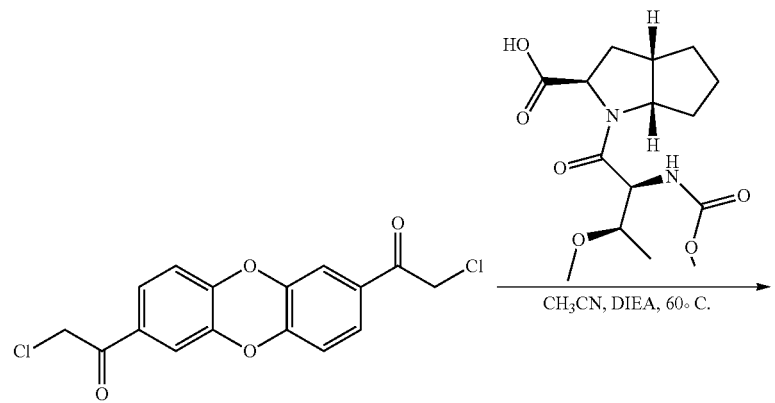
Intermediate 1
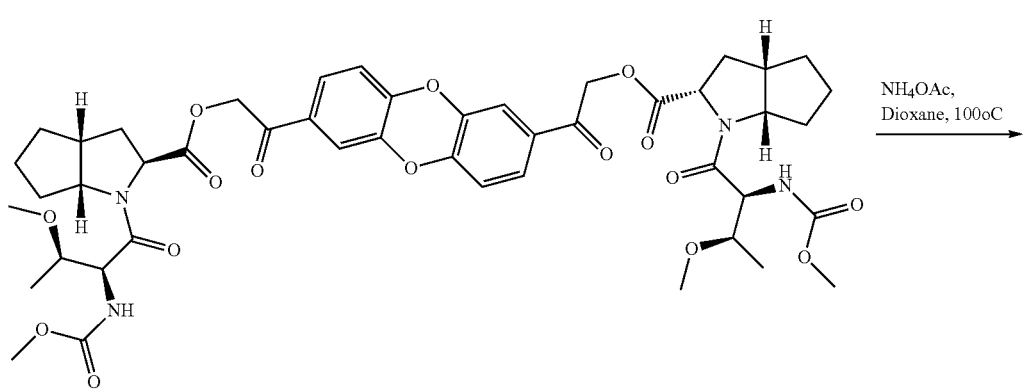
Intermediate 2
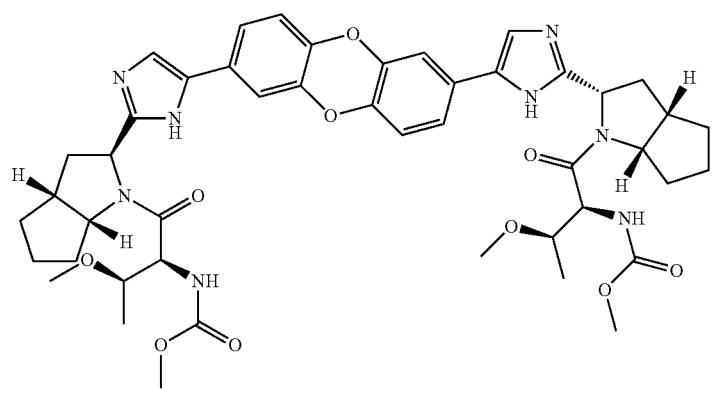
Example 10

Intermediate 1: 1,1'-(dibenzo[b,e][1,4]dioxine-2,7-diyl)bis(2-chloroethanone)

Dibenzo[b,e][1,4]dioxine (2 g, 10.86 mmol), was taken in dichloromethane (10 ml), 2-chloroacetyl chloride (2.0 ml, 24.97 mmol) was added and the reaction was cooled to −78° C. Aluminium chloride (5.79 g, 43.4 mmol) was added carefully and was stirred for additional 2 h at −78° C., then slowly allowed to reach rt and stirred for additional 2 h. Cooled to 0° C. and ice was added, stirred for few min, white precipitation noticed, MeOH (5 mL) was added and stirred for 1 h. The precipitate was filtered and washed with water and used in the next step. Yield: 1.8, 50%; ES LC-MS m/z=337 (M−H$^+$);

Intermediate 2: (S,R,2S,2'S,3aS,3a'S,6aS,6a'S)-dibenzo[b,e][1,4]dioxine-2,7-diylbis(2-oxoethane-2,1-diyl)bis(1-((2S,3R)-3-methoxy-2-((methoxycarbonyl)amino)butanoyl)octahydrocyclopenta[b]pyrrole-2-carboxylate)

Under N$_2$ atmosphere, to a stirred suspension of 1,1'-(dibenzo[b,e][1,4]dioxine-2,7-diyl)bis(2-chloroethanone) (130 mg, 0.270 mmol) in acetonitrile (5.00 mL) was added (2S,3aS,6aS)-1-((2S,3R)-3-methoxy-2-((methoxycarbonyl)amino)butanoyl)octahydrocyclopenta[b]pyrrole-2-carboxylic acid (177 mg, 0.540 mmol) followed by addition of DIEA (0.094 mL, 0.540 mmol). The mixture was stirred at 60° c. for 12 h. After evaporation of solvent the material was used in the next step. Small amount was subjected to HPLC purification to provide two product in ~4:1 ratio as a mixture of intermediate 2 and other regiomer.

Yield: 130 mg, 52%; ES LC-MS m/z=921.3 (M−H$^+$);
$^1$H NMR (400 MHz, DMSO-d6) δ: 7.65-7.76 (m, 3H), 7.52-7.63 (m, 2H), 7.07-7.29 (m, 2H), 5.49-5.61 (m, 2H), 5.39 (d, J=16.9 Hz, 2H), 4.77 (d, J=6.1 Hz, 2H), 4.59 (t, J=8.3 Hz, 2H), 4.23 (t, J=8.5 Hz, 2H), 3.33 (s, 12H), 3.23 (s, 6H), 2.80 (br. s., 2H), 2.09 (br. s., 2H), 1.85-1.94 (m, 2H), 1.79 (br. s., 5H), 1.55 (br. s., 4H), 1.05 (d, J=5.9 Hz, 6H).

Example 10

Dimethyl ((2S,2'S,3R,3'R)-((2S,2'S,3aS,3a'S,6aS,6a'S)-2,2'-(5,5'-(dibenzo[b,e][1,4]dioxine-2,7-diyl)bis(1H-imidazole-5,2-diyl))bis(hexahydrocyclopenta[b]pyrrole-2,1(2H)-diyl))bis(3-methoxy-1-oxobutane-2,1-diyl))dicarbamate To a stirred solution of (S,R,2S,2'S,3aS,3a'S,6aS,6a'S)-dibenzo[b,e][1,4]dioxine-2,7-diylbis(2-oxoethane-2,1-diyl)bis(1-((2S,3R)-3-methoxy-2-((methoxycarbonyl)amino)butanoyl)octahydrocyclopenta[b]pyrrole-2-carboxylate) (130 mg, 0.141 mmol) in 1,4-Dioxane (5 mL) in a sealed tube was added ammonium acetate (416 mg, 5.40 mmol). The reaction mixture was refluxed at 100° C. for 10 h. Cooled down to rt, filtered off excess of ammonium acetate. The filtrate was evaporated and the residue was purified by column (ISCO—silica gel, 0-15% methanol in ethyl acetate) and then by HPLC (ACN:H$_2$O-0.1% NH$_4$OH) to give the product as a solid.

Yield: 30 mg, 25%; ES LC-MS m/z=881.4 (M−H$^+$);
$^1$H NMR (400 MHz, DMSO-d6) δ: 11.61-12.20 (m, 2H), 7.52-7.65 (m, 2H), 7.45 (d, J=1.8 Hz, 2H), 7.32-7.36 (m, 2H), 7.27-7.31 (m, 2H), 6.97 (d, J=8.3 Hz, 2H), 5.10 (t, J=7.5 Hz, 2H), 4.82 (d, J=7.7 Hz, 2H), 4.28 (t, J=8.4 Hz, 2H), 3.56 (s, 5H), 3.43-3.50 (m, 2H), 3.41 (s, 1H), 3.31 (s, 1H), 3.25-3.28 (m, 2H), 3.22 (s, 4H), 2.67-2.83 (m, 2H), 2.39 (dt, J=13.1, 8.8 Hz, 2H), 2.14 (br. s., 3H), 1.91-2.03 (m, 2H), 1.86 (d, J=12.2 Hz, 2H), 1.69-1.81 (m, 2H), 1.45-1.67 (m, 3H), 1.20-1.32 (m, 1H), 1.08 (d, J=6.1 Hz, 6H).

Protocol for Testing and Data Analysis of Compounds in the HCV Replicon Assay

Compounds were assayed for activity against HCV using the genotype 1a and 1b subgenomic replicon model systems. Stable cell lines bearing the genotype 1a and 1b replicons were used for screening of compounds. Both replicons are bicistronic and contain the firefly luciferase gene. The ET cell line is stably transfected with RNA transcripts harboring a I$_{389}$luc-ubi-neo/NS3-3'/ET replicon with firefly luciferase-ubiquitin-neomycin phosphotransferase fusion protein and EMCV-IRES driven NS3-5B polyprotein containing the cell culture adaptive mutations (E1202G; T1280I; K1846T) (Krieger at al, 2001 and unpublished). The genotype 1a replicon is a stable cell line contains the H77 NS3-5B polyprotein sequence, modified to contain the firefly luciferase gene and encode for neomycin resistance. The genotype 1a replicon contains several adaptive changes (NS4B Q31H, NS5A K68R, NS5A S232I). The cells were grown in DMEM, supplemented with 10% fetal calf serum, 2 mM Glutamine, Penicillin (100 IU/mL)/Streptomycin (100 μg/mL), 1x non-essential amino acids, and 250-500 μg/mL G418 ("Geneticin"). They were all available through Life Technologies (Bethesda, Md.). The cells were plated at 5×10$^3$ cells/well in 384 well plates containing compounds. The final concentration of compounds ranged between 0.03 pM to 50 μm and the final DMSO concentration of 0.5-1%.

Luciferase activity was measured 48 hours later by adding a Steady glo reagent (Promega, Madison, Wis.). Percent inhibition of replication data was plotted relative to no compound control. Under the same condition, cytotoxicity of the compounds was determined using cell titer glo (Promega, Madison, Wis.). EC50s were determined from an 11 point dose response curve using 3-4-fold serial dilution for each compound, which spans a concentration range >1000 fold. The level of inhibition for each compound was determined with Activity Base or with BioAssay plus the Excel XC50 module. Percent inhibition was determined with the following equation where the cross-talk corrected value is the value from the test well, the compound positive control mean is the average value of the wells with no compound present, and the DMSO negative control mean is the average value of the wells with DMSO but no cells present.

$$100 * (1 - \frac{\text{(Cross-talk corrected value} - \text{Compound Positive Control Mean))}}{\text{DMSO Negative Control Mean} - \text{Compound Positive Control Mean}}$$

These normalized values are exported to EC$_{50}$ where they are plotted against the molar compound concentrations using the standard four parameter logistic equation:

$$y = A + \frac{B - A}{1 + \left[\frac{10^x}{10^c}\right]^D}$$

Where:
A=minimum y   D=slope factor
B=maximum y   x=log$_{10}$ compound concentration [M]
C=log$_{10}$EC$_{50}$   pEC$_{50}$=−C The results of the assay are summarized below.

| Example | Replicon 1A EC$_{50}$ | Replicon 1B EC$_{50}$ |
|---|---|---|
| Example 1 | 11 pM | 6 pM |
| Example 2 | 10 pM | 8 pM |
| Example 3 | 13 pM | 8 pM |
| Example 4 | 40 pM | 20 pM |
| Example 5 | 32 pM | 20 pM |
| Example 6 | 16 pM | 16 pM |
| Example 7 | 160 pM | 32 pM |
| Example 8 | 32 pM | 16 pM |
| Example 9 | 80 pM | 32 pM |
| Example 10 | 10 pM | 10 pM |

What is claimed is:

1. A compound or pharmaceutically acceptable salt of Formula I;

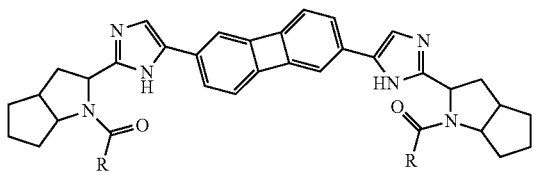
I wherein each R is independently —CH(R$^1$)—NH—C(O)—OR$^2$;

wherein each R$^1$ is independently —CH(OH)—CH$_3$ or —CH(OCH$_3$)—CH$_3$; and each R$^2$ is independently C$_{1-3}$alkyl.

2. A compound according to claim 1 wherein each R$^1$ group is enantiomerically enriched with the enantiomer where the chiral carbon to which R$^1$ is bonded has an absolute configuration of S.

3. A compound according to claim 1 wherein each R$^1$ group is enantiomerically enriched with the enantiomer where the chiral carbon in each R$^1$ group has an absolute configuration of R.

4. A compound according to claim 1 wherein each R$^2$ is methyl.

5. A pharmaceutically acceptable salt of a compound according to claim 1.

6. A pharmaceutical composition comprising a compound or salt according to claim 1.

7. A method for treating a viral infection in a human comprising administration of a pharmaceutical composition according to claim 6.

8. The method of claim 7 wherein said viral infection is an HCV infection.

9. The compound

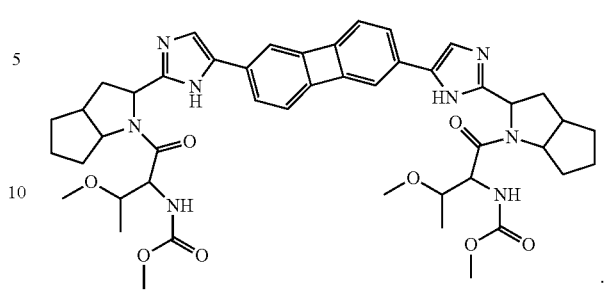

10. The compound of claim 9 wherein said compound is enantiomerically enriched in the compound having the following stereochemistry

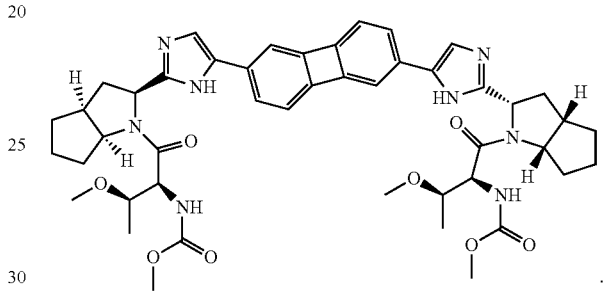

11. A pharmaceutically acceptable salt of the compound of claim 9.

12. A pharmaceutical composition comprising the compound of claim 9 or a pharmaceutically acceptable salt thereof.

13. A method for treating a viral infection in a human comprising administration of a pharmaceutical composition according to claim 12.

14. A compound or pharmaceutically acceptable salt of Formula II or Formula III;

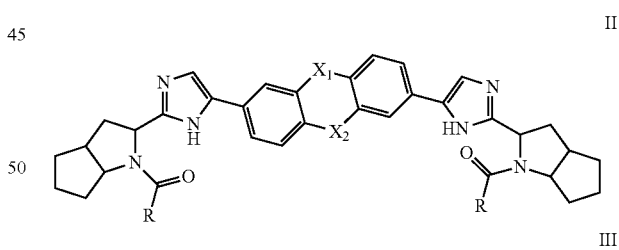
II

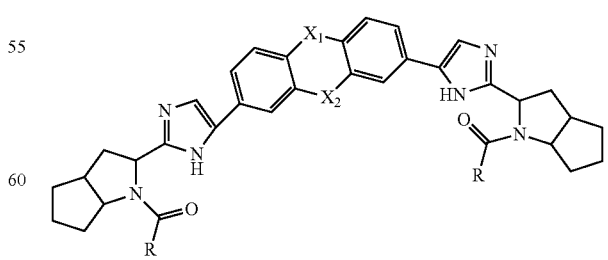
III wherein X$^1$ and X$^2$ are independently O, SO$_2$, NCH$_3$, CF$_2$, CH$_2$, CH$_2$CH$_2$, or a bond (i.e. absent); and each R is independently —CH(R$^1$)—NH—C(O)—OR$^2$;

wherein each $R^1$ is independently —CH(OH)—CH$_3$ or —CH(OCH$_3$)—CH$_3$; and each $R^2$ is independently C$_{1-3}$alkyl.

15. A pharmaceutically acceptable salt of a compound according to claim 14.

16. A pharmaceutical composition comprising a compound according to claim 14 or a pharmaceutically acceptable salt thereof.

17. A method for treating a viral infection in a human comprising administration of a pharmaceutical composition of claim 16.

* * * * *